United States Patent
Lee et al.

(10) Patent No.: US 10,112,959 B2
(45) Date of Patent: Oct. 30, 2018

(54) METAL COMPLEX AND COLOR CONVERSION FILM COMPRISING SAME

(71) Applicant: LG CHEM, LTD., Seoul (KR)

(72) Inventors: Hoyong Lee, Daejeon (KR); Kichul Koo, Daejeon (KR); Minyoung Kang, Daejeon (KR); Duy Hieu Le, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/529,046

(22) PCT Filed: Oct. 26, 2015

(86) PCT No.: PCT/KR2015/011332
§ 371 (c)(1),
(2) Date: May 23, 2017

(87) PCT Pub. No.: WO2016/108411
PCT Pub. Date: Jul. 7, 2016

(65) Prior Publication Data
US 2017/0260212 A1    Sep. 14, 2017

(30) Foreign Application Priority Data
Dec. 29, 2014  (KR) ........................ 10-2014-0192221

(51) Int. Cl.
*C07F 5/02* (2006.01)
*F21V 9/30* (2018.01)
*F21K 9/64* (2016.01)
*C08K 5/55* (2006.01)

(52) U.S. Cl.
CPC ................ *C07F 5/022* (2013.01); *C07F 5/02* (2013.01); *C08K 5/55* (2013.01); *F21K 9/64* (2016.08); *F21V 9/30* (2018.02)

(58) Field of Classification Search
CPC .... C07F 5/022; C07F 5/02; F21V 9/30; F21V 9/64; C08K 5/55
USPC ........................................................... 524/105
See application file for complete search history.

(56) References Cited

U.S. PATENT DOCUMENTS

| | | | |
|---|---|---|---|
| 2011/0226992 A1* | 9/2011 | Takeshima | C09K 11/06 252/301.16 |
| 2016/0121002 A1* | 5/2016 | Meimetis | C07F 5/022 424/9.6 |

FOREIGN PATENT DOCUMENTS

| | | | | |
|---|---|---|---|---|
| JP | 2005-154534 A | 6/2005 | | |
| JP | 201018788 A | 1/2010 | | |
| JP | 2013-105665 A | 5/2013 | | |
| WO | 2009/116456 A1 | 9/2009 | | |
| WO | WO-2009116456 A1 * | 9/2009 | ............... | C07F 5/02 |
| WO | 2010/032453 A1 | 3/2010 | | |
| WO | 2014/182704 A2 | 11/2014 | | |

OTHER PUBLICATIONS

Jillian G. Baker et al., "Synthesis and Characterization of High-Affinity 4,4-Difluoro-4-bora-3a,4a-diaza-s-indacene-Labeled Fluorescent Ligands for Human ß-Adrenoceptors", Journal of Medicinal Chemistry, vol. 54, Issue 19, Aug. 29, 2011, pp. 6874-6887.

* cited by examiner

*Primary Examiner* — Michael Bernshteyn
(74) *Attorney, Agent, or Firm* — Dentons US LLP

(57) ABSTRACT

The present disclosure relates to a novel compound, a color conversion film, a backlight unit and a display device comprising the same.

13 Claims, 6 Drawing Sheets

[FIG. 1]
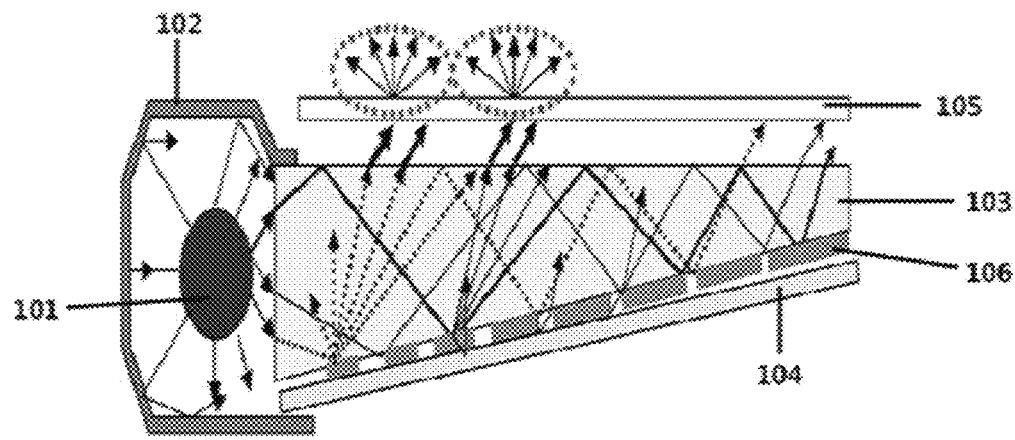
[FIG. 2]
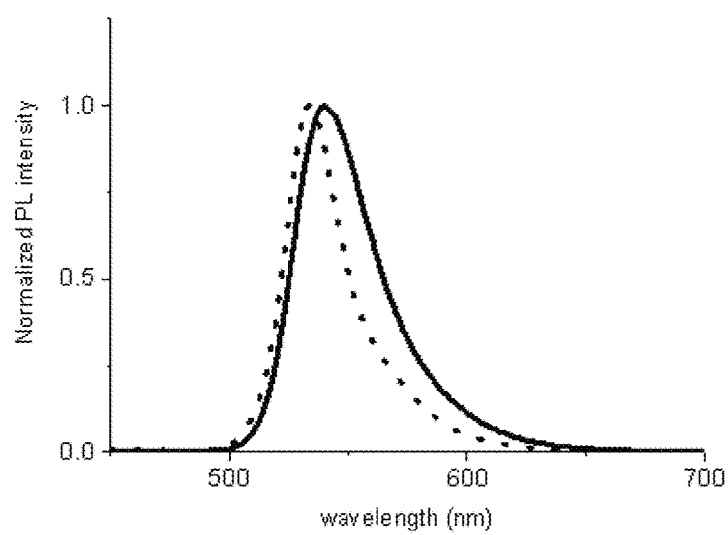

[FIG. 3]
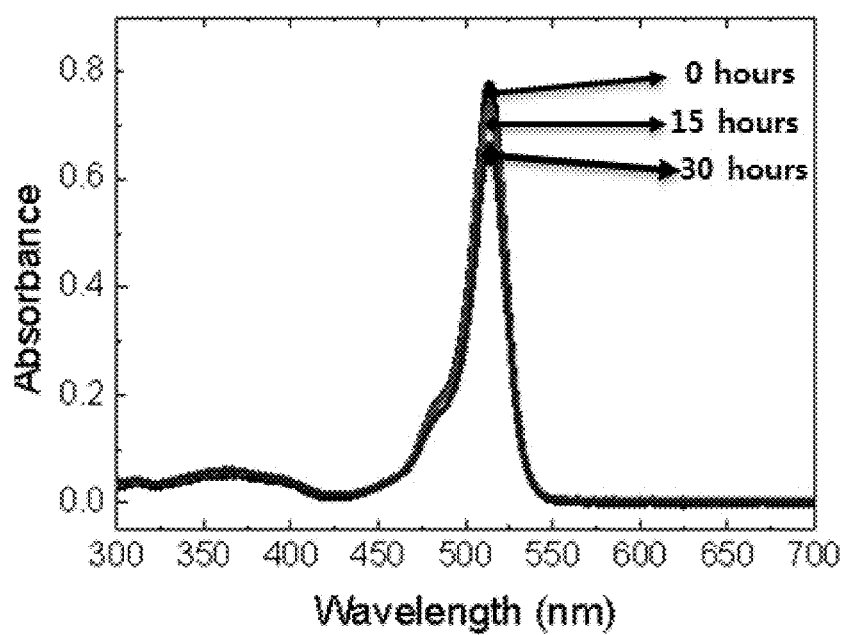

[FIG. 4]
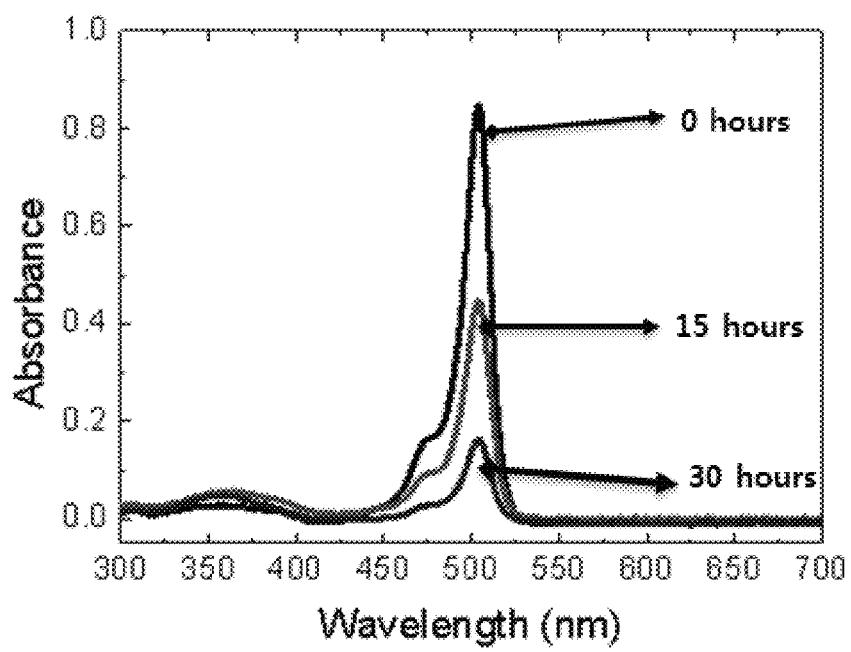

[FIG. 5]
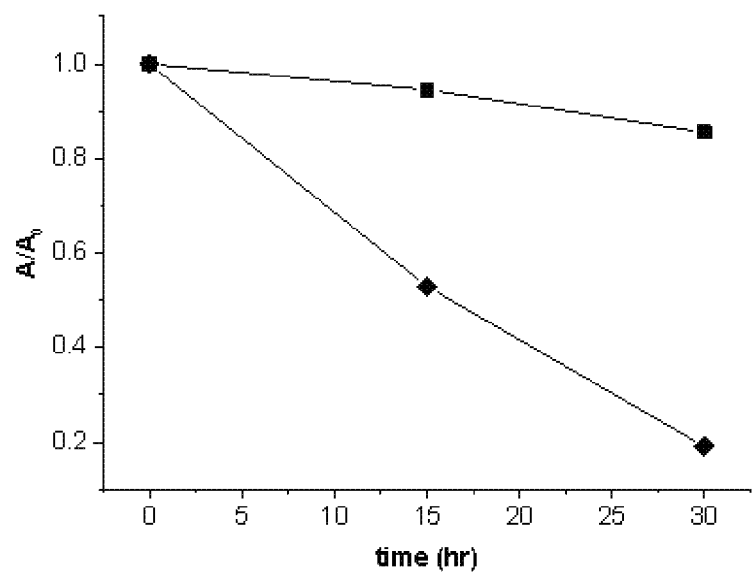
[FIG. 6]
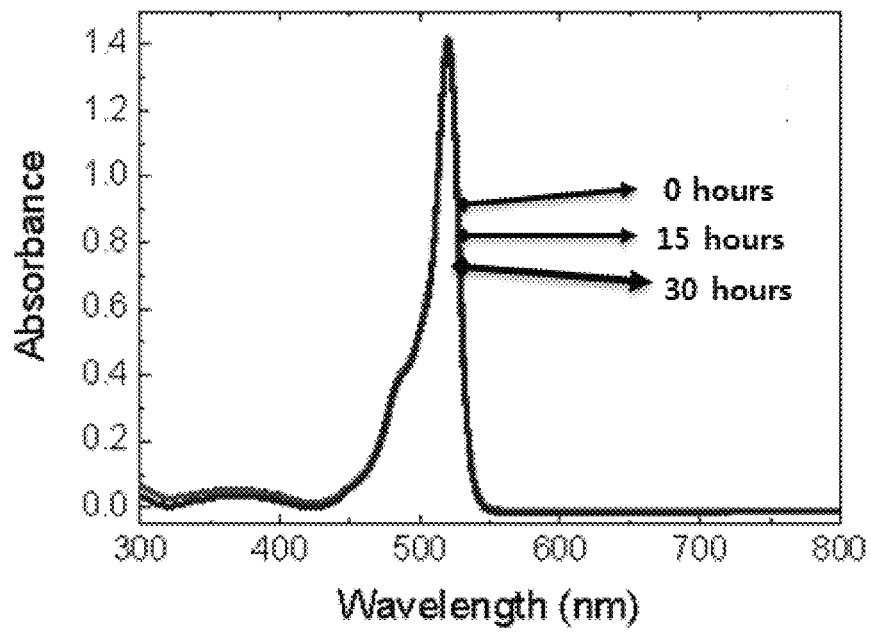

[FIG. 7]
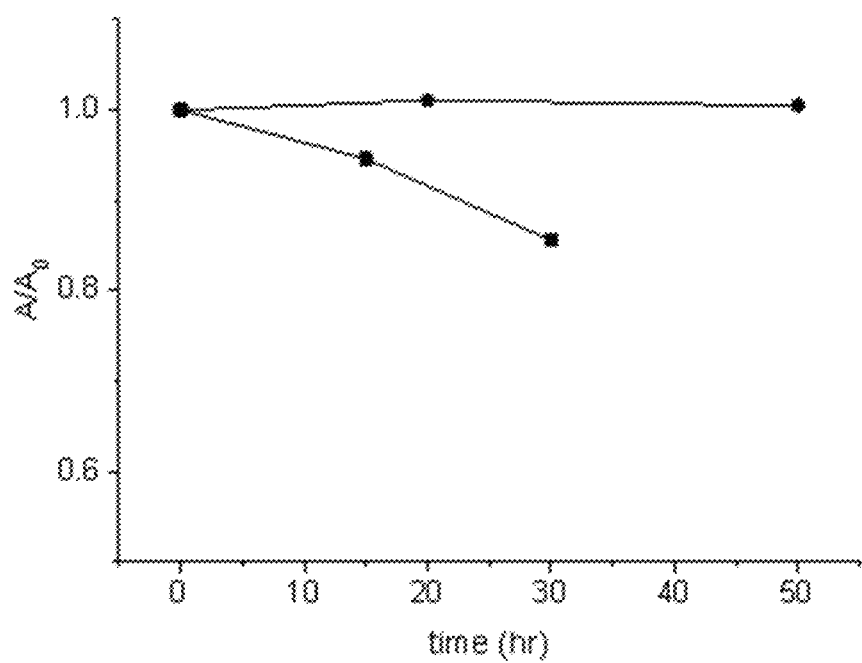

[FIG. 8]
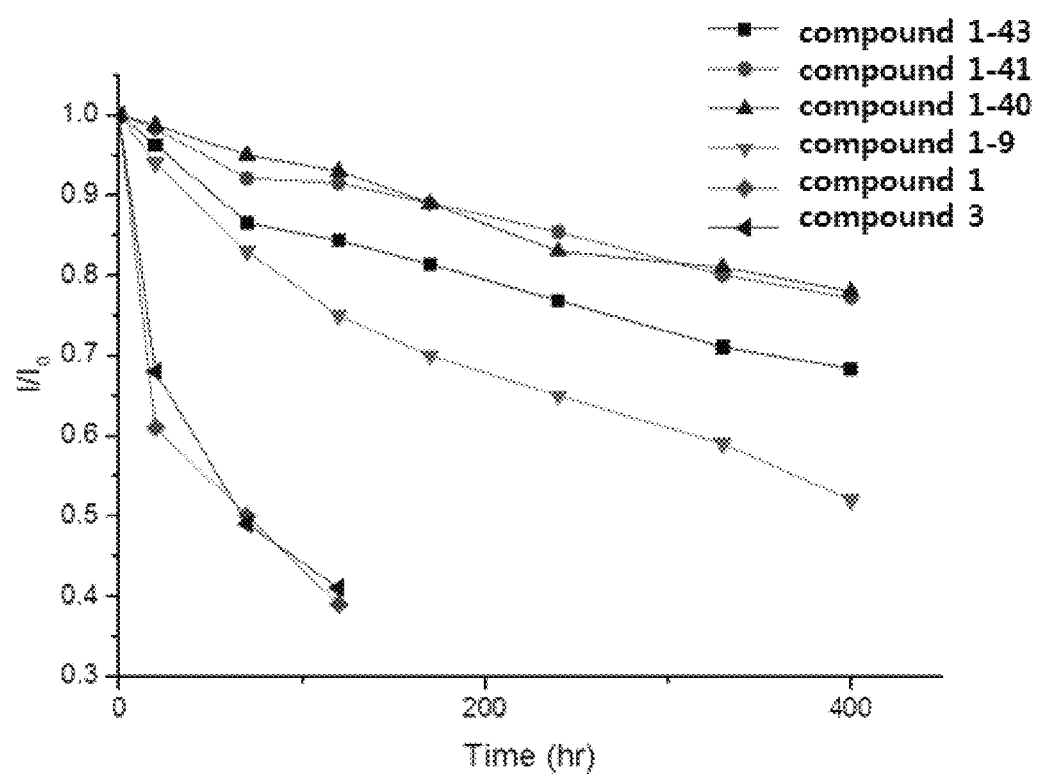

METAL COMPLEX AND COLOR CONVERSION FILM COMPRISING SAME

TECHNICAL FIELD

This application is a National Stage Application of International Application No. PCT/KR2015/011332 filed on Oct. 26, 2015, which claims the benefit of Korean Patent Application No. 10- 2014-0192221 filed on Dec. 29, 2014, all of which are hereby incorporated by reference in their entirety for all purposes as if fully set forth herein.

The present application relates to a novel metal complex and a color conversion film comprising the same. In addition, the present application relates to a backlight unit and a display device including the color conversion film.

BACKGROUND ART

Existing light emitting diodes (LED) are obtained either by mixing a green phosphorescent substance and a red phosphorescent substance to a blue light emitting diode, or mixing a yellow phosphorescent substance and a blue-green phosphorescent substance to a UV-light emission light emitting diode. However, such a method is difficult to control colors and accordingly, color rendering is not favorable. As a result, Color Gamut is inferior.

In order to overcome such Color Gamut decline, and reduce production costs, a method obtaining green and red by filming quantum dots and binding the result to a blue LED has been recently tried. However, cadmium series quantum dots have safety problems, and other quantum dots have significantly lower efficiency than cadmium series. In addition, quantum dots have a disadvantage in that they have inferior stability for oxygen and water, and when aggregated, the performance significantly declines. Furthermore, unit production costs are high since maintaining constant sizes is difficult when quantum dots are produced.

PRIOR ART DOCUMENTS

Patent Documents

Korean Patent Application Laid-Open Publication No. 2000-0011622.

DISCLOSURE

Technical Problem

The present application provides a novel metal complex and a color conversion film comprising the same. In addition, the present application provides a backlight unit and a display device including the color conversion film.

Technical Solution

One embodiment of the present application provides a compound of the following Chemical Formula 1.

[Chemical Formula 1]

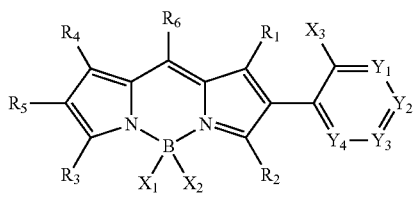

In Chemical Formula 1, at least one of $R_1$ to $R_5$ is selected from among the following structural formulae,

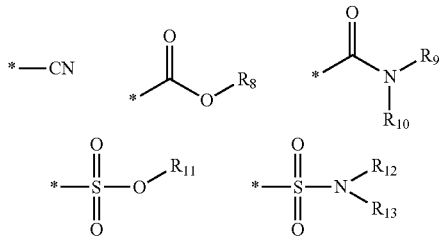

$R_6$ is hydrogen; a nitrile group; a substituted or unsubstituted alkyl group; a substituted or unsubstituted cycloalkyl group; a substituted or unsubstituted alkoxy group; a substituted or unsubstituted aryl group; a substituted or unsubstituted alkylaryl group; or a substituted or unsubstituted aromatic or aliphatic heterocyclic group, $X_1$ and $X_2$ are the same as or different from each other, and each independently F; a nitrile group; a substituted or unsubstituted alkynyl group; a substituted or unsubstituted alkyl group; a substituted or unsubstituted alkoxy group; a substituted or unsubstituted aryloxy group; a substituted or unsubstituted arylalkoxy group; a substituted or unsubstituted aryl group; or a substituted or unsubstituted aromatic or aliphatic heterocyclic group, or bond to each other to form an aromatic or aliphatic ring, $X_3$ is a halogen group; a nitrile group; a carbonyl group; an ester group; an amide group; a sulfonate group; a substituted or unsubstituted alkyl group; a fluoroalkyl group; a substituted or unsubstituted cycloalkyl group; a substituted or unsubstituted alkoxy group; a substituted or unsubstituted alkylsulfoxy group; a substituted or unsubstituted silyl group; a substituted or unsubstituted phosphine oxide group; or a substituted or unsubstituted alkylaryl group, $Y_1$ is $CR_{101}$ or N, $Y_2$ is $CR_{102}$ or N, $Y_3$ is $CR_{103}$ or N and $Y_4$ is $CR_{104}$ or N, and groups of $R_1$ to $R_5$ that are not the above-mentioned structural formulae, $R_8$ to $R_{13}$ and $R_{101}$ to $R_{104}$ are the same as or different from each other, and each independently hydrogen; deuterium; a halogen group; a nitrile group; a nitro group; a carbonyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted arylalkyl group; a substituted or unsubstituted alkylaryl group; a substituted or unsubstituted aryl group; or a substituted or unsubstituted aromatic or aliphatic heterocyclic group, and $R_9$ and $R_{10}$ may bond to each other to form an aliphatic or aromatic ring, and $R_{12}$ and $R_{13}$ may bond to each other to form an aliphatic or aromatic ring.

Another embodiment of the present application provides a color conversion film including a resin matrix; and the compound of Chemical Formula 1 dispersed into the resin matrix.

Still another embodiment of the present application provides a backlight unit including the color conversion film.

Yet still another embodiment of the present application provides a display device including the backlight unit.

Advantageous Effects

A metal complex described in the present specification has a substituent ($X_3$) at the ortho position, and provides a green fluorescent substance having a small half-width and thereby having high efficiency. When the metal complex does not have a substituent ($X_3$) at the ortho position, a light emission wavelength is red-shifted, which is not suitable as a green fluorescent substance, and causes a problem of an efficiency decrease due to a half-width increase. In addition, in the metal complex described in the present specification, an electron-withdrawing group is introduced to at least one of $R_1$ to $R_5$, and therefore, the metal complex lowers oxidation potential and thereby lowers reactivity with singlet oxygen, and as a result, light stability in a color conversion film that does not use a barrier film significantly increases. Accordingly, by using the metal complex described in the present specification as a fluorescent material of a color conversion film, a color conversion film having excellent luminance and Color Gamut, and having a simple manufacturing process and low unit manufacturing costs by not using a barrier film can be provided.

DESCRIPTION OF DRAWINGS

FIG. 1 is a mimetic diagram using a color conversion film according to one embodiment of the present application to a backlight.

FIG. 2 shows light emission spectra (toluene $1 \times 10^{-5}$ M) of Compound 1 (dotted line) and Compound 2 (straight line).

FIGS. 3, 4 and 6 show changes in UV-vis spectra of Compound 1, Compound 3 and Compound 1-40 by time under blue light, respectively.

FIG. 5 shows absorbance variation in maximum absorption wavelengths of Compound 1 and Compound 3 by time.

FIG. 7 shows absorbance variation in maximum absorption wavelengths of Compound 1 and Compound 1-40 by time.

FIG. 8 shows intensity variation in green fluorescence of a color conversion film prepared using Compound 1, Compound 3, Compound 1-9, Compound 1-40, Compound 1-41 or Compound 1-43 by time under the driving of a blue backlight.

MODE FOR DISCLOSURE

One embodiment of the present application provides a compound of the following Chemical Formula 1:

[Chemical Formula 1]

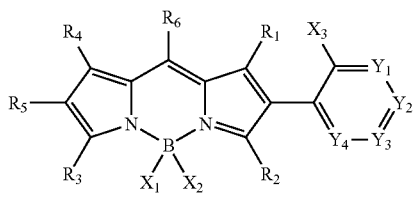

In Chemical Formula 1, at least one of $R_1$ to $R_5$ is selected from among the following structural formulae,

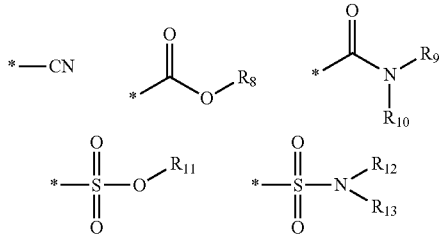

$R_6$ is hydrogen; a nitrile group; a substituted or unsubstituted alkyl group; a substituted or unsubstituted cycloalkyl group; a substituted or unsubstituted alkoxy group; a substituted or unsubstituted aryl group; a substituted or unsubstituted alkylaryl group; or a substituted or unsubstituted aromatic or aliphatic heterocyclic group, $X_1$ and $X_2$ are the same as or different from each other, and each independently F; a nitrile group; a substituted or unsubstituted alkynyl group; a substituted or unsubstituted alkyl group; a substituted or unsubstituted alkoxy group; a substituted or unsubstituted aryloxy group; a substituted or unsubstituted arylalkoxy group; a substituted or unsubstituted aryl group; or a substituted or unsubstituted aromatic or aliphatic heterocyclic group, or bond to each other to form an aromatic or aliphatic ring, $X_3$ is a halogen group; a nitrile group; a carbonyl group; an ester group; an amide group; a sulfonate group; a substituted or unsubstituted alkyl group; a fluoroalkyl group; a substituted or unsubstituted cycloalkyl group; a substituted or unsubstituted alkoxy group; a substituted or unsubstituted alkylsulfoxy group; a substituted or unsubstituted silyl group; a substituted or unsubstituted phosphine oxide group; or a substituted or unsubstituted alkylaryl group, $Y_1$ is $CR_{101}$ or N, $Y_2$ is $CR_{102}$ or N, $Y_3$ is $CR_{103}$ or N and $Y_4$ is $CR_{104}$ or N, and groups of $R_1$ to $R_5$ that are not the above-mentioned structural formulae, $R_8$ to $R_{13}$ and $R_{101}$ to $R_{104}$ are the same as or different from each other, and each independently hydrogen; deuterium; a halogen group; a nitrile group; a nitro group; a carbonyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted arylalkyl group; a substituted or unsubstituted alkylaryl group; a substituted or unsubstituted aryl group; or a substituted or unsubstituted aromatic or aliphatic heterocyclic group, and $R_9$ and $R_{10}$ may bond to each other to form an aliphatic or aromatic ring, and $R_{12}$ and $R_{13}$ may bond to each other to form an aliphatic or aromatic ring.

The compound of Chemical Formula 1 has a substituent ($X_3$) at the pyrromethane metal complex core, and provides a fluorescent substance having a small half-width and thereby having high efficiency. In addition, in the compound of Chemical Formula 1, a specific type of an electron-withdrawing group is introduced to at least one of $R_1$ to $R_5$ and therefore, the compound of Chemical Formula 1 lowers oxidation potential and thereby lowers reactivity with singlet oxygen, and as a result, light stability in a color conversion film that does not use a barrier film is significantly enhanced. Accordingly, by using the metal complex described in the present specification as a fluorescent material of a color conversion film, a color conversion film having excellent luminance and Color Gamut, and having a simple manufacturing process and low unit manufacturing costs by not using a barrier film can be provided.

The compound of Chemical Formula 1 may absorb blue light and release green light depending on a substituent.

According to one example, the compound of Chemical Formula 1 has a maximum light emission peak present in 520 nm to 550 nm in a film state. Such a compound emits green light.

According to one example, the compound of Chemical Formula 1 has a maximum light emission peak present in 520 nm to 550 nm in a film state, and a half-width of the light emission peak is 50 nm or less. Having such a small half-width may further increase Color Gamut. Herein, the light emission peak of the compound of Chemical Formula 1 may have a half-width of 5 nm or more.

According to one example, the compound of Chemical Formula 1 has a maximum light emission peak present in 610 nm to 650 nm in a film state. Such a compound emits red light.

According to one example, the compound of Chemical Formula 1 has a maximum light emission peak present in 610 nm to 650 nm in a film state, and a half-width of the light emission peak is 60 nm or less. Having such a small half-width may further increase Color Gamut. Herein, the light emission peak of the compound of Chemical Formula 1 may have a half-width of 5 nm or more.

According to one example, the compound of Chemical Formula 1 has quantum efficiency of 0.9 or more.

In the present specification, a "film state" means a state prepared in a film form instead of a solution state, using the compound of Chemical Formula 1 alone, or as a mixture with other components that do not affect half-width and quantum efficiency measurements.

In the present specification, the half-width means a width of a light emission peak at half the maximum height in a maximum light emission peak of light emitting from the compound of Chemical Formula 1.

In the present specification, the quantum efficiency may be measured using methods known in the art, and for example, may be measured using an integrating sphere.

Examples of the substituents of Chemical Formula 1 are described below, however, the substituents are not limited thereto.

The term "substituted or unsubstituted" in the present specification means being substituted with one or more substituents selected from the group consisting of deuterium; a halogen group; a nitrile group; a nitro group; a carbonyl group; a carboxyl group; an ester group; an imide group; an amide group; a sulfonate group; a substituted or unsubstituted alkynyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted arylalkyl group; a substituted or unsubstituted alkylaryl group; a substituted or unsubstituted aryl group; or a substituted or unsubstituted aromatic or aliphatic heterocyclic group including one or more of N, O and S atoms, or having no substituents, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

The term "substitution" means a hydrogen atom bonding to a carbon atom of a compound is changed to another substituent, and the position of substitution is not limited as long as it is a position at which a hydrogen atom is substituted, that is, a position at which a substituent may substitute, and when two or more substituents substitute, the two or more substituents may be the same as or different from each other.

In the present specification, examples of the halogen group include fluorine, chlorine, bromine or iodine.

In the present specification, in the carbonyl group, (—C=O) may be substituted with a substituted or unsubstituted alkyl group, a substituted or unsubstituted arylalkyl group, a substituted or unsubstituted alkylaryl group, or a substituted or unsubstituted aryl group.

In the present specification, in the ester group, oxygen of the ester group may be substituted with a substituted or unsubstituted alkyl group, a substituted or unsubstituted arylalkyl group, a substituted or unsubstituted alkylaryl group, or a substituted or unsubstituted aryl group. Specifically, compounds having the following structural formulae may be included, but the compound is not limited thereto.

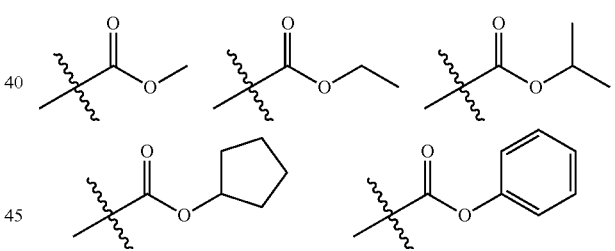

In the present specification, the number of carbon atoms of the imide group is not particularly limited, but is preferably 1 to 25. Specifically, compounds having the following structures may be included, but the compound is not limited thereto.

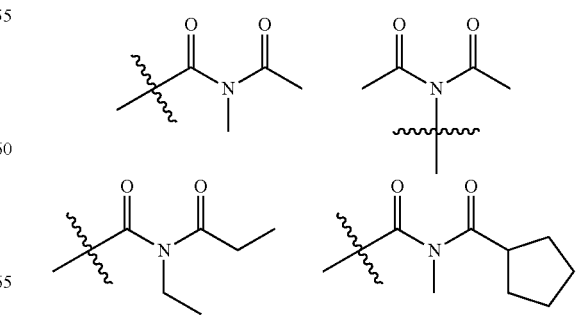

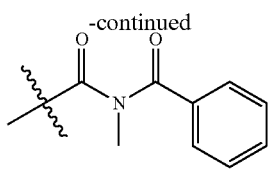

In the present specification, in the amide group, nitrogen of the amide group may be once or twice substituted with hydrogen, a substituted or unsubstituted alkyl group, a substituted or unsubstituted arylalkyl group, a substituted or unsubstituted alkylaryl group, or a substituted or unsubstituted aryl group. Specifically, compounds having the following structural formulae may be included, but the compound is not limited thereto.

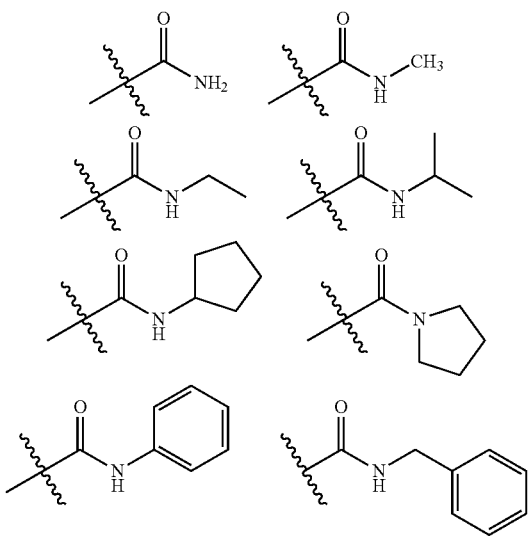

In the present specification, the sulfonate group may be expressed as —SO₃X, and X may be hydrogen or a group 1 element. For example, the sulfonate group includes —SO₃Na.

In the present specification, the alkynyl group may be linear or branched, and although not particularly limited thereto, the number of carbon atoms is preferably 2 to 50.

In the present specification, the alkyl group may be linear or branched, and the number of carbon atoms is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the aryl group may be a monocyclic aryl group or a multicyclic aryl group, and includes cases substituted with an alkyl group having 1 to 25 carbon atoms or an alkoxy group having 1 to 25 carbon atoms. In addition, the aryl group in the present specification may mean an aromatic ring.

When the aryl group is a monocyclic aryl group, the number of carbon atoms is not particularly limited, but is preferably 6 to 25. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably 10 to 24. Specific example of the multicyclic aryl group may include a naphthyl group, an anthryl group, a phenanthryl group, a pyrenyl group, a perylenyl group, a crycenyl group, a fluorenyl group and the like, but are not limited thereto.

In the present specification, the fluorenyl group may be substituted, and adjacent substituents may bond to each other to form a ring.

When the fluorenyl group is substituted,

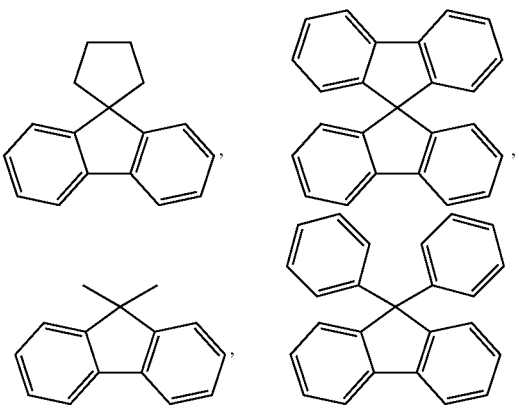

and the like may be included. However, the structure is not limited thereto.

In the present specification, the silyl group may be expressed as —SiRR'R", and R, R' and R" may be each independently hydrogen, a linear, branched or cyclic alkyl group having 1 to 25 carbon atoms, or an aryl group having 6 to 25 carbon atoms. Specific examples thereof include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be expressed as —BRR', and R and R' may be each independently hydrogen, a linear, branched or cyclic alkyl group having 1 to 25 carbon atoms, or an aryl group having 6 to 25 carbon atoms.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include a monocyclic aryl group, a multicyclic aryl group, or both a monocyclic aryl group and a multicyclic aryl group.

In the present specification, the heterocyclic group is a heterocyclic group including one or more of O, N and S as a heteroatom, and although not particularly limited thereto, the number of carbon atoms is preferably 2 to 60. Examples of the heterocyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the aryl group in the arylalkyl group, the alkylaryl group, the arylalkoxy group, the aryloxy group, the arylthioxy group, the arylsulfoxy group and the aralkylamine group is the same as the examples of the aryl group described above. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, examples of the arylthioxy group include a phenylthioxy group, a 2-methylphenylthioxy group, a 4-tert-butylphenylthioxy group and the like, and examples of the arylsulfoxy group include a benzenesulfoxy group, a p-toluenesulfoxy group and the like, but the examples are not limited thereto.

In the present specification, the alkyl group in the arylalkyl group, the alkylaryl group, the alkylthioxy group and the alkylsulfoxy group is the same as the examples of the alkyl group described above. Specific examples of the alkylthioxy group include a methylthioxy group, an ethylthioxy group, a tert-butylthioxy group, a hexylthioxy group, an octylthioxy group and the like, and examples of the alkylsulfoxy group include a methylsulfoxy group, an ethylsulfoxy group, a propylsulfoxy group, a butylsulfoxy group and the like, but the examples are not limited thereto.

In the present specification, the alkoxy group in the arylalkoxy group is the same as the examples of the alkoxy group described above.

According to one embodiment of the present application, $R_1$ to $R_4$ of Chemical Formula 1 are the same as or different from each other, and each independently hydrogen, deuterium, a substituted or unsubstituted alkyl group, a substituted or unsubstituted alkylaryl group, a substituted or unsubstituted arylalkyl group, a substituted or unsubstituted aryl group, or one of the following structural formulae.

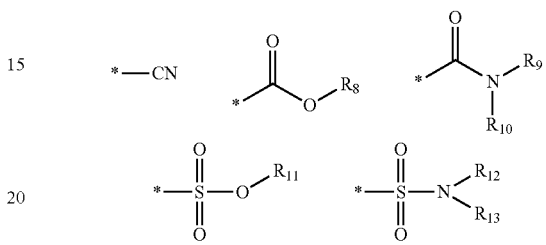

Definitions of $R_8$ to $R_{13}$ are the same as those described above.

According to one embodiment of the present application, $R_1$ to $R_4$ of Chemical Formula 1 are the same as or different from each other, and each independently hydrogen, deuterium, a substituted or unsubstituted alkyl group, a substituted or unsubstituted alkylaryl group, a substituted or unsubstituted arylalkyl group, or a substituted or unsubstituted aryl group.

According to one embodiment of the present application, $R_1$ to $R_4$ of Chemical Formula 1 are the same as or different from each other, and each independently hydrogen, deuterium, an alkyl group unsubstituted or substituted with a halogen group, an alkylaryl group, an arylalkyl group, or an aryl group.

According to one embodiment of the present application, $R_1$ to $R_4$ of Chemical Formula 1 are the same as or different from each other, and each independently an alkyl group unsubstituted or substituted with fluorine, an alkylaryl group, an arylalkyl group, or an aryl group.

According to one embodiment of the present application, $R_1$ to $R_4$ of Chemical Formula 1 are the same as or different from each other, and each independently a methyl group unsubsituted or substituted with fluorine; a t-butyl group; a phenyl group unsubstituted or substituted with a group selected from the group consisting of a methyl group, a t-butyl group and a methoxy group; a biphenyl group unsubstituted or substituted with a t-butyl group.

According to one embodiment of the present application, at least one of $R_1$ to $R_4$ of Chemical Formula 1 is one of the following structural formulae.

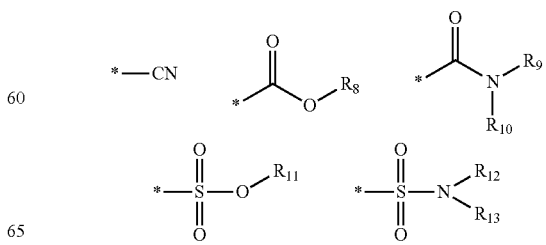

Definitions of $R_8$ to $R_{13}$ are the same as those described above.

According to one embodiment of the present application, $R_1$ and $R_2$ are the same, and $R_3$ and $R_4$ are the same in Chemical Formula 1.

According to one embodiment of the present application, $R_1$ and $R_2$ are the same, $R_3$ and $R_4$ are the same, and $R_1$ and $R_4$ are different in Chemical Formula 1.

According to one embodiment of the present application, $R_1$ and $R_4$ are the same, and $R_2$ and $R_3$ are the same in Chemical Formula 1.

According to one embodiment of the present application, $R_1$ and $R_4$ are the same, $R_2$ and $R_3$ are the same, and $R_1$ and $R_2$ are different in Chemical Formula 1.

According to one embodiment of the present application, $R_1$ to $R_4$ of Chemical Formula 1 are the same.

According to one embodiment of the present application, $R_5$ of Chemical Formula 1 is hydrogen, deuterium, or one of the following structural formulae.

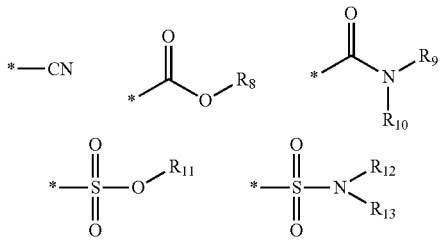

Definitions of $R_8$ to $R_{13}$ are the same as those described above.

According to one embodiment of the present application, $R_6$ of Chemical Formula 1 is hydrogen; a substituted or unsubstituted alkyl group; a substituted or unsubstituted cycloalkyl group; a substituted or unsubstituted alkoxy group; a substituted or unsubstituted aryl group; a substituted or unsubstituted alkylaryl group; or a substituted or unsubstituted aromatic or aliphatic heterocyclic group.

According to one embodiment of the present application, $R_6$ of Chemical Formula 1 is hydrogen; a nitrile group; an alkyl group unsubstituted or substituted with a halogen group or an aryl group; a cycloalkyl group; an alkoxy group; an aryl group unsubstituted or substituted with a group selected from the group consisting of a halogen group, a nitrile group, an ester group, an alkynyl group, an alkyl group, an alkoxy group, an aryloxy group and an aryl group, or substituted with a group bonding two or more selected from the group described above; or an aromatic or aliphatic heterocyclic group unsubstituted or substituted with a group selected from the group consisting of a halogen group, a nitrile group, an ester group, an alkynyl group, an alkyl group, an alkoxy group, an aryloxy group and an aryl group, or substituted with a group bonding two or more selected from the group described above.

According to one embodiment of the present application, $R_6$ of Chemical Formula 1 is hydrogen; a nitrile group; a methyl group substituted with a halogen group or an aryl group; a propyl group substituted with a halogen group; a cyclohexyl group; a propoxy group; a phenyl group unsubstituted or substituted with a group selected from the group consisting of a halogen group, a nitrile group, an ester group, an alkynyl group, an alkyl group, an alkoxy group, an aryloxy group and an aryl group, or substituted with a group bonding two or more selected from the group described above; a biphenyl group unsubstituted or substituted with a group consisting of a halogen group, a nitrile group, an ester group, an alkynyl group, an alkyl group, an alkoxy group, an aryloxy group and an aryl group, or substituted with a group bonding two or more selected from the group described above; a terphenyl group unsubstituted or substituted with a group consisting of a halogen group, a nitrile group, an ester group, an alkynyl group, an alkyl group, an alkoxy group, an aryloxy group and an aryl group, or substituted with a group bonding two or more selected from the group described above; or a dibenzofuran group unsubstituted or substituted with a group consisting of a halogen group, a nitrile group, an ester group, an alkynyl group, an alkyl group, an alkoxy group and an aryl group, or substituted with a group bonding two or more selected from the group described above.

According to one embodiment of the present application, $R_6$ of Chemical Formula 1 is hydrogen; a nitrile group; a methyl group substituted with fluorine or a phenyl group; a propyl group substituted with fluorine; a cyclohexyl group; a propoxy group; a phenyl group unsubstituted or substituted with a group selected from the group consisting of a methyl group, a pentyloxy group substituted with a carboxyl group, an ethoxy group substituted with an ethoxy group substituted with a methoxy group, a methoxy group, a dibenzofuran group, a terphenyl group substituted with a t-butyl group, a terphenyl group substituted with a carboxyl group, and a propylester group; a biphenyl group unsubstituted or substituted with a group selected from the group consisting of a nitrile group, a methyl group, a phenyl group substituted with a t-butyl group, and a phenyl group substituted with a carboxyl group; or a terphenyl group unsubstituted or substituted with a group selected from the group consisting of a methyl group, a t-butyl group, a phenyl group substituted with a t-butyl group, a carboxyl group, and a phenyl group substituted with a carboxyl group.

According to one embodiment of the present application, $R_8$ and $R_{11}$ are the same as or different from each other, and each independently hydrogen; deuterium; a substituted or unsubstituted alkyl group; a substituted or unsubstituted cycloalkyl group; a substituted or unsubstituted arylalkyl group; a substituted or unsubstituted alkylaryl group; a substituted or unsubstituted aryl group; or a substituted or unsubstituted aromatic or aliphatic heterocyclic group.

According to one embodiment of the present application, $R_8$ and $R_{11}$ are the same as or different from each other, and each independently a substituted or unsubstituted alkyl group; a substituted or unsubstituted cycloalkyl group; a substituted or unsubstituted arylalkyl group; a substituted or unsubstituted alkylaryl group; a substituted or unsubstituted aryl group; or a substituted or unsubstituted aromatic or aliphatic heterocyclic group.

According to one embodiment of the present application, $R_8$ and $R_{11}$ are the same as or different from each other, and each independently a substituted or unsubstituted alkyl group; a substituted or unsubstituted cycloalkyl group; a substituted or unsubstituted arylalkyl group; a substituted or unsubstituted alkylaryl group; a substituted or unsubstituted aryl group; or a substituted or unsubstituted aromatic or aliphatic heterocyclic group, and when these are substituted, the substituent is a group selected from the group consisting of a halogen group; a nitrile group; a carboxyl group; an ester group; an alkyl group; a cycloalkyl group; an alkoxy group; an aryloxy group; an arylalkyl group; an alkylaryl group; an aryl group; or an aromatic and aliphatic heterocyclic group, or a group bonding two or more of the groups selected from the group described above.

According to one embodiment of the present application, $R_8$ and $R_{11}$ are the same as or different from each other, and each independently an alkyl group unsubstituted or substituted with a group selected from the group consisting of a halogen group, a nitrile group, a carboxyl group, an aryl group and a heterocyclic group; an alkylaryl group; a heterocyclic group substituted with an aryl group.

According to one embodiment of the present application, $R_8$ and $R_{11}$ are the same as or different from each other, and each independently a methyl group unsubstituted or substituted with a group selected from the group consisting of a phenyl group, a biphenyl group, a phenyl group substituted with a naphthyl group, a phenyl group substituted with a dibenzofuran group, a phenyl group substituted with fluorine, a phenyl group substituted with a trifluoromethyl group, a phenyl group substituted with an anthracene group substituted with a phenyl group, a phenyl group substituted with a nitrile group, and a phenyl group substituted with a carboxyl group; an ethyl group unsubstituted or substituted with a group selected from the group consisting of a phenoxy group substituted with an anthracene group substituted with a phenyl group, a carboxyl group, a phenothiazine group, a naphthyloxy group, a triazineoxy group substituted with a phenyl group, and a pyrimidineoxy group substituted with a phenyl group; an n-propyl group; an n-butyl group unsubstituted or substituted with fluorine; a pentyl group unsubstituted or substituted with fluorine; a phenyl group unsubstituted or substituted with a group selected from the group consisting of a t-butyl group and a methyl group; a naphthyl group; or a carbazolyl group unsubstituted or substituted with a phenyl group.

According to one embodiment of the present application, $R_9$ and $R_{10}$ are the same as or different from each other, and each independently hydrogen; deuterium; a substituted or unsubstituted alkyl group; a substituted or unsubstituted cycloalkyl group; a substituted or unsubstituted arylalkyl group; a substituted or unsubstituted alkylaryl group; a substituted or unsubstituted aryl group; or a substituted or unsubstituted aromatic or aliphatic heterocyclic group, or bond to each other to form an aliphatic or aromatic ring.

According to one embodiment of the present application, $R_9$ and $R_{10}$ are the same as or different from each other, and each independently hydrogen; deuterium; an alkyl group; a cycloalkyl group; an arylalkyl group unsubstituted or substituted with halogen or a haloalkyl group; an alkylaryl group; an aryl group unsubstituted or substituted with halogen or a haloalkyl group; or an aromatic and aliphatic heterocyclic group, or bond to each other to form an aliphatic ring.

According to one embodiment of the present application, $R_9$ and $R_{10}$ are the same as or different from each other, and each independently hydrogen; or a methyl group substituted with a phenyl group substituted with a trifluoromethyl group, or may bond to each other to form a phenothiazine ring.

According to one embodiment of the present application, $R_{12}$ and $R_{13}$ are the same as or different from each other, and each independently hydrogen; deuterium; a substituted or unsubstituted alkyl group; a substituted or unsubstituted cycloalkyl group; a substituted or unsubstituted arylalkyl group; a substituted or unsubstituted alkylaryl group; a substituted or unsubstituted aryl group; or a substituted or unsubstituted aromatic or aliphatic heterocyclic group, or bond to each other to form an aliphatic or aromatic ring.

According to one embodiment of the present application, $R_{12}$ and $R_{13}$ are the same as or different from each other, and each independently hydrogen; deuterium; an alkyl group; a cycloalkyl group; an arylalkyl group unsubstituted or substituted with halogen or a haloalkyl group; an alkylaryl group; an aryl group unsubstituted or substituted with halogen or a haloalkyl group; or an aromatic and aliphatic heterocyclic group, or bond to each other to form an aliphatic ring.

According to one embodiment of the present application, $X_1$ and $X_2$ are the same as or different from each other, and each independently F; a nitrile group; a substituted or unsubstituted alkynyl group; a substituted or unsubstituted alkyl group; a substituted or unsubstituted alkoxy group; a substituted or unsubstituted aryloxy group; a substituted or unsubstituted aryl group; or a substituted or unsubstituted aromatic or aliphatic heterocyclic group, or bond to each other to form an aromatic or aliphatic ring.

According to one embodiment of the present application, $X_1$ and $X_2$ are the same as or different from each other, and each independently F; a nitrile group; an alkynyl group unsubstituted or substituted with an aryl group or an alkylaryl group; an alkoxy group unsubstituted or substituted with a halogen group; an aryl group unsubstituted or substituted with a halogen group or a heterocyclic group; or an aromatic or aliphatic heterocyclic group unsubstituted or substituted with an aryl group, or bond to each other to form a monocyclic or multicyclic aromatic or aliphatic ring.

According to one embodiment of the present application, $X_1$ and $X_2$ are the same as or different from each other, and each independently F; a nitrile group; an ethynyl group substituted with a triiso-propylsilyl group; or an ethynyl group substituted with a phenyl group substituted with a t-butyl group.

According to one embodiment of the present application, $X_3$ is a halogen group; a nitrile group; an ester group; an alkyl group; an alkoxy group substituted with a fluoro group; or a fluoroalkyl group.

According to one embodiment of the present application, $X_3$ is F; a nitrile group; a methoxy group; a trifluoromethyl group; a methylester group; or an n-butoxy group substituted with a fluoro group.

According to one embodiment of the present application, $Y_1$ to $Y_4$ are the same as or different from each other, and each independently CH, CF or N.

According to one embodiment of the present application, $R_{101}$ to $R_{104}$ are the same as or different from each other, and each independently hydrogen; deuterium; a halogen group; a nitrile group; an ester group; a substituted or unsubstituted alkyl group; a substituted or unsubstituted alkylaryl group; a substituted or unsubstituted arylalkyl group; or a substituted or unsubstituted aryl group.

According to one embodiment of the present application, $R_{101}$ to $R_{104}$ are the same as or different from each other, and each independently hydrogen; deuterium; a halogen group; a nitrile group; an ester group; an alkyl group unsubstituted or substituted with halogen; an alkylaryl group; an arylalkyl group; or an aryl group.

According to one embodiment of the present application, $R_{101}$ to $R_{104}$ are the same as or different from each other, and each independently hydrogen; or F.

According to one embodiment of the present application, Chemical Formula 1 may be represented by one of the following structural formulae.

Chemical Formula 1-1
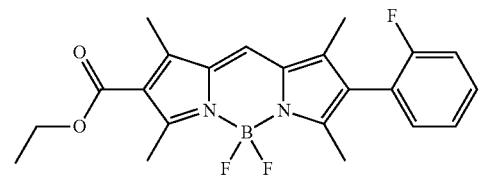
Chemical Formula 1-2
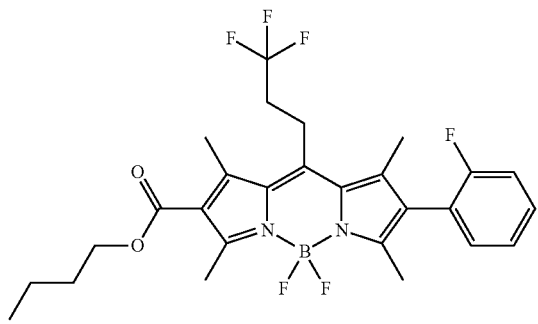
Chemical Formula 1-3
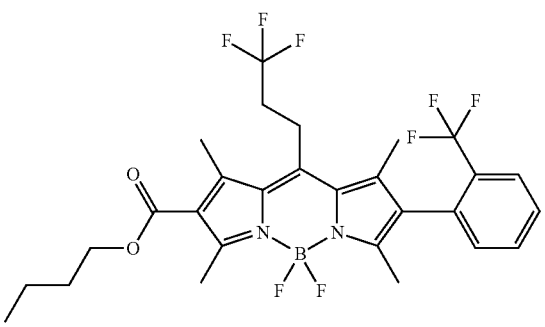
Chemical Formula 1-4
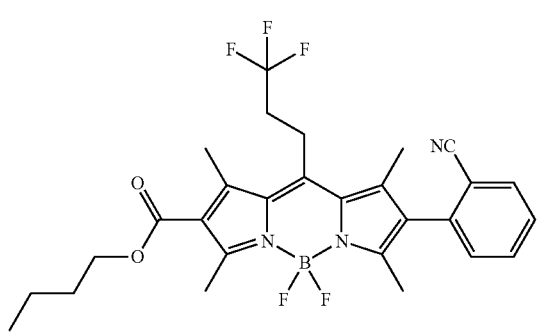
Chemical Formula 1-5
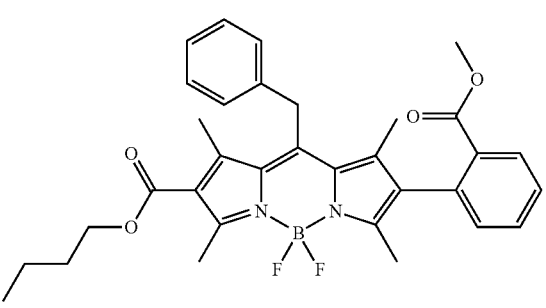
-continued
Chemical Formula 1-6
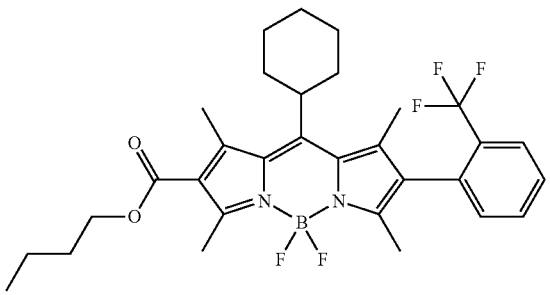
Chemical Formula 1-7
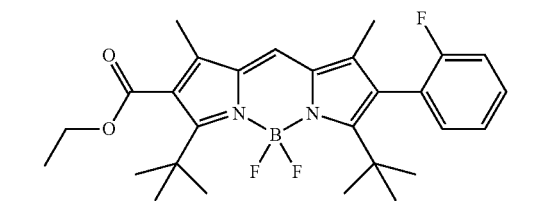
Chemical Formula 1-8
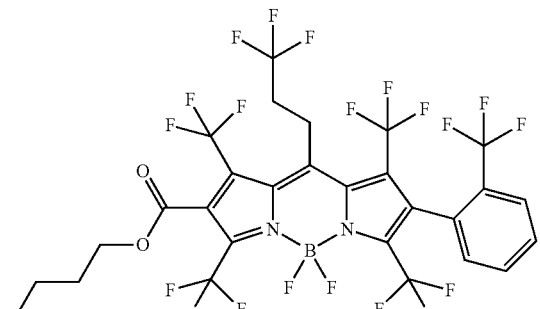
Chemical Formula 1-9
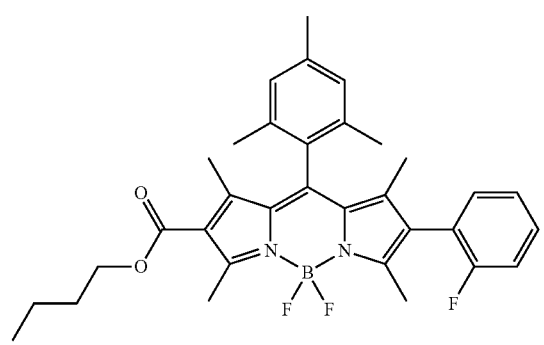
Chemical Formula 1-10
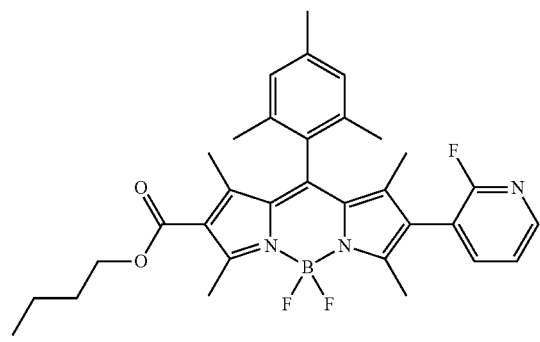

Chemical Formula 1-11
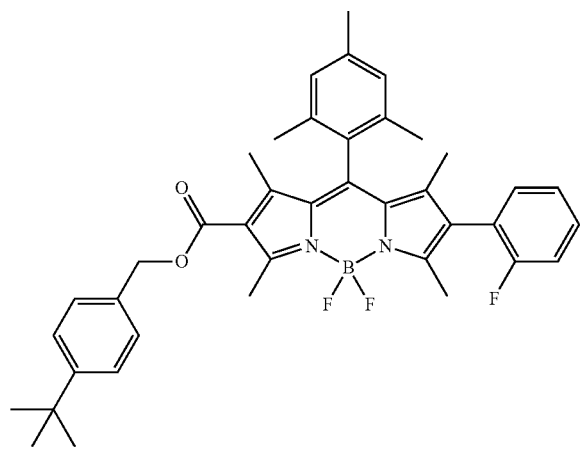
Chemical Formula 1-12
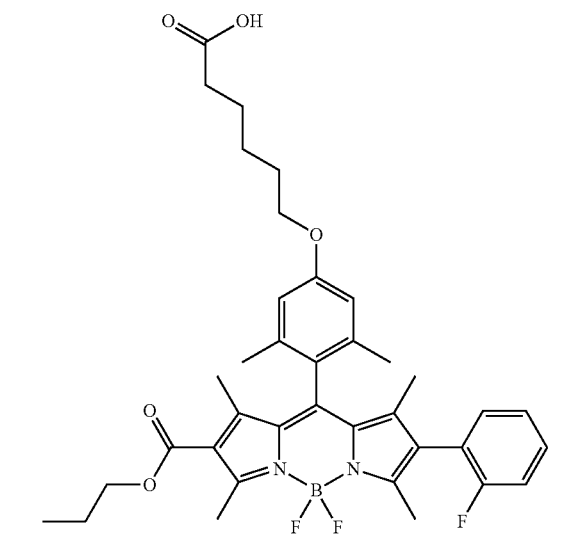
Chemical Formula 1-13
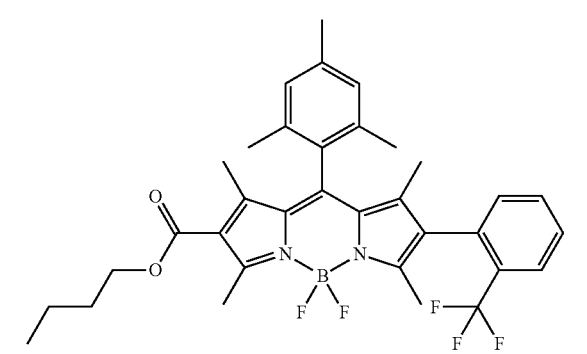
Chemical Formula 1-14
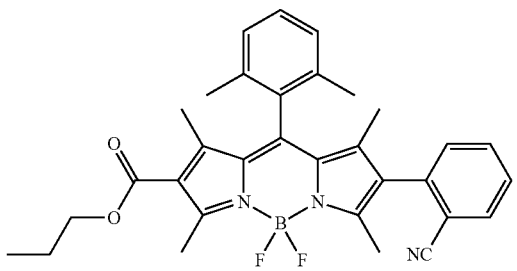
Chemical Formula 1-15
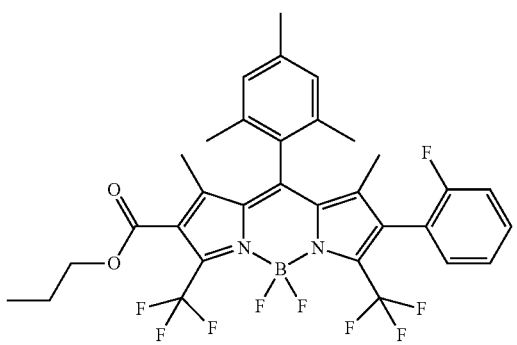
Chemical Formula 1-16
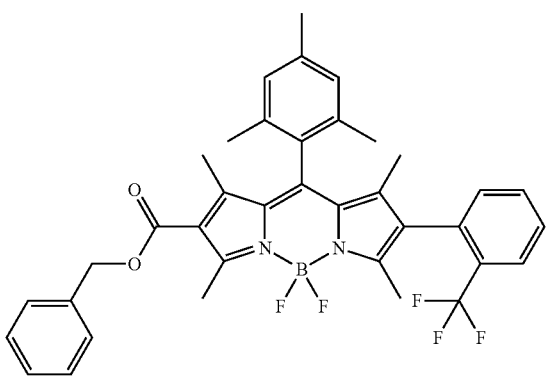
Chemical Formula 1-17
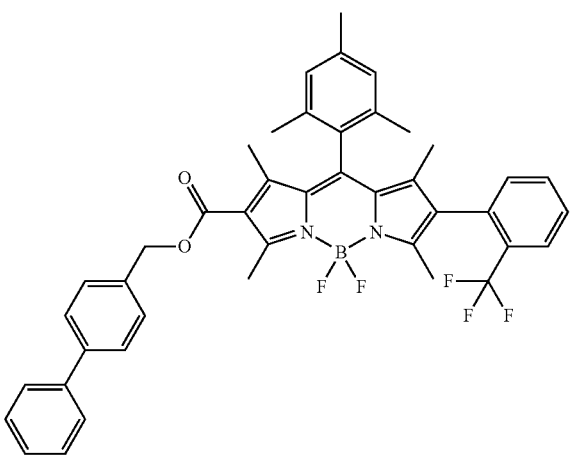

Chemical Formula 1-18
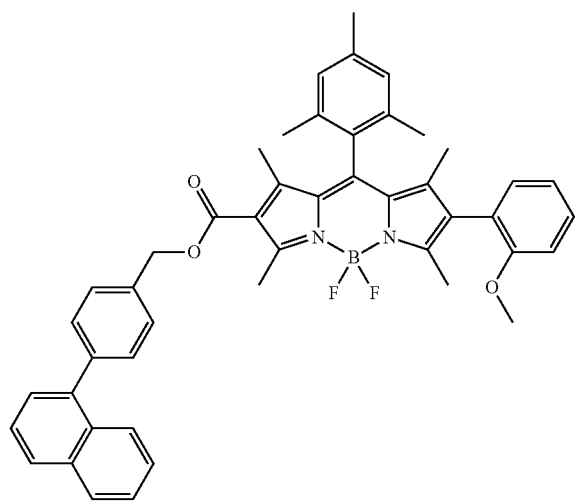
Chemical Formula 1-19
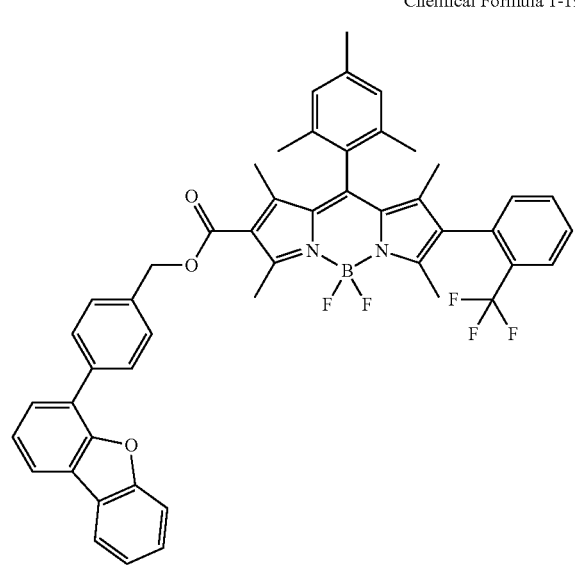
Chemical Formula 1-20
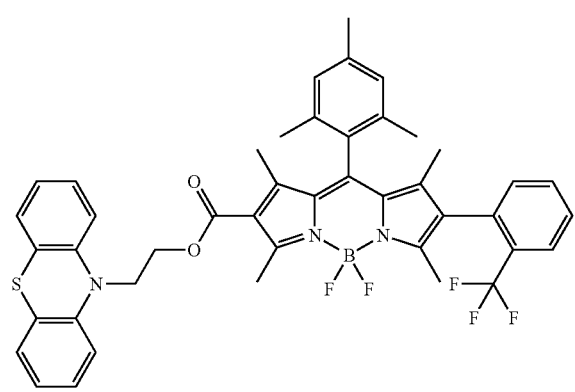
Chemical Formula 1-21
Chemical Formula 1-22
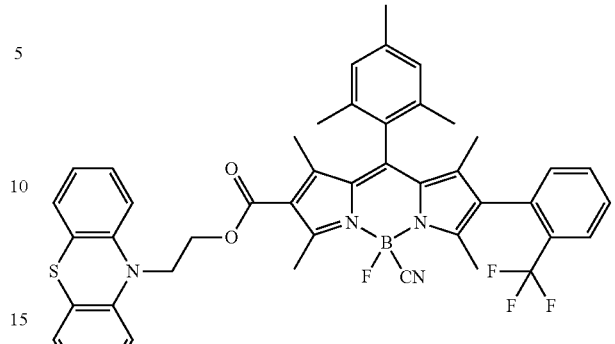
Chemical Formula 1-23

Chemical Formula 1-24
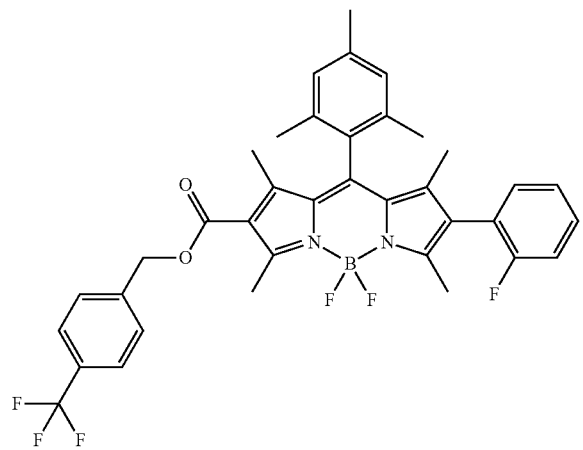
Chemical Formula 1-25
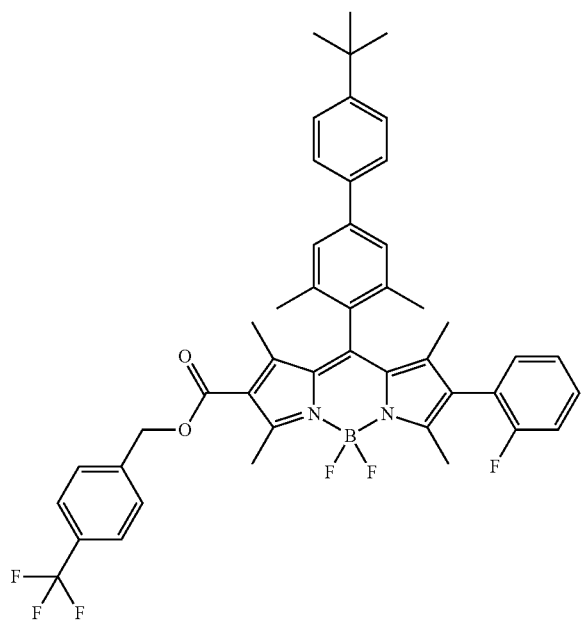
Chemical Formula 1-26
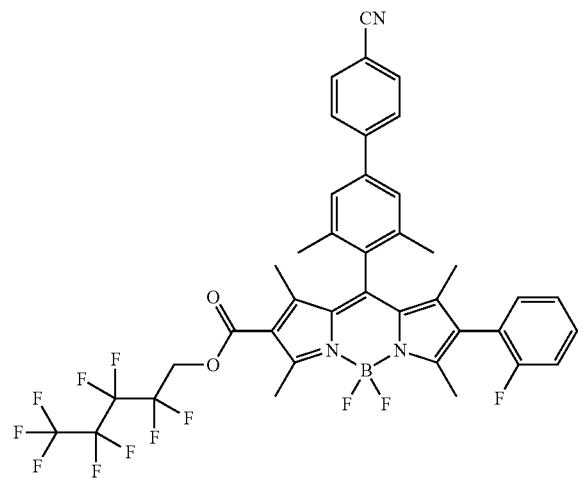
Chemical Formula 1-27
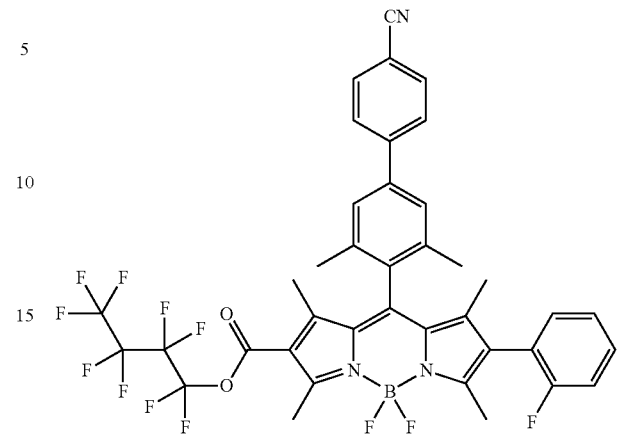
Chemical Formula 1-28
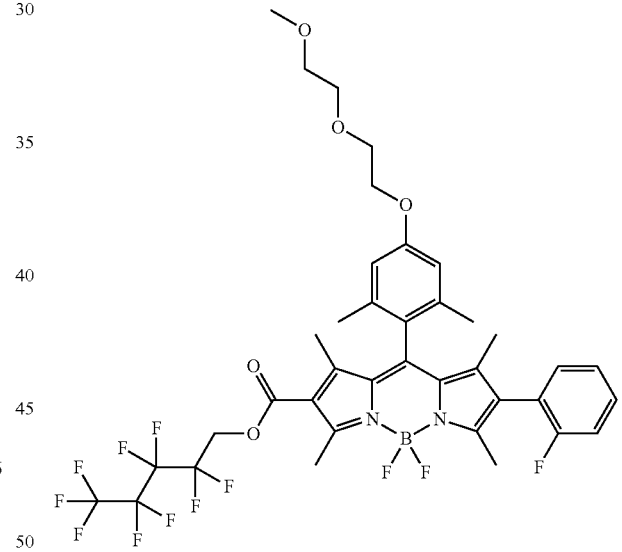
Chemical Formula 1-29
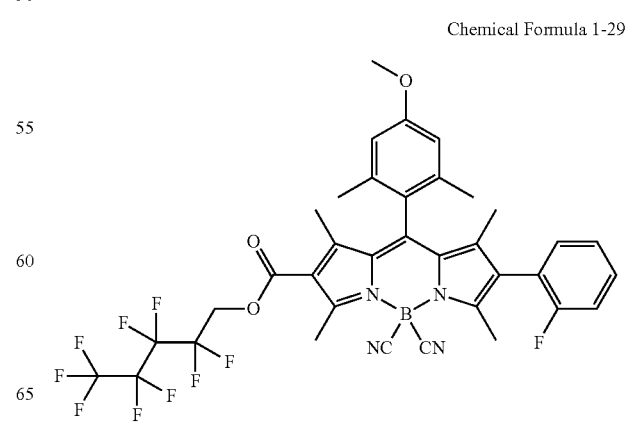

Chemical Formula 1-30
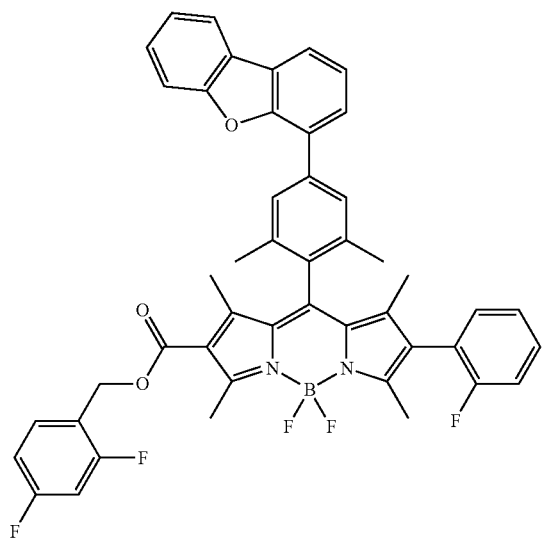
Chemical Formula 1-31
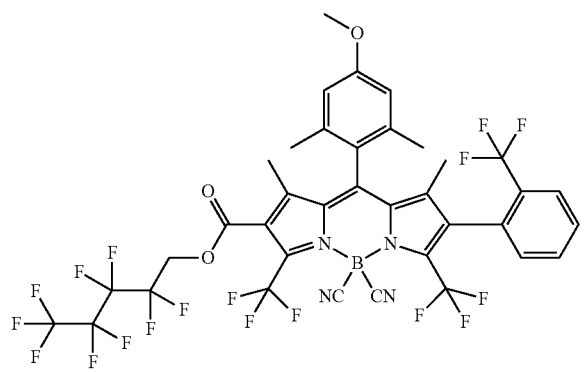
Chemical Formula 1-32
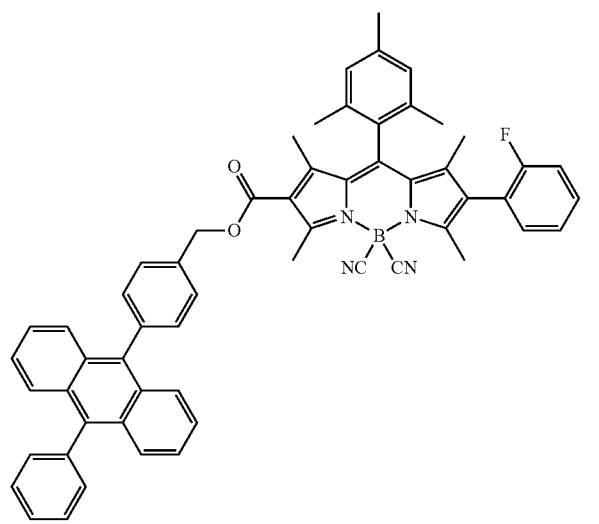
Chemical Formula 1-33
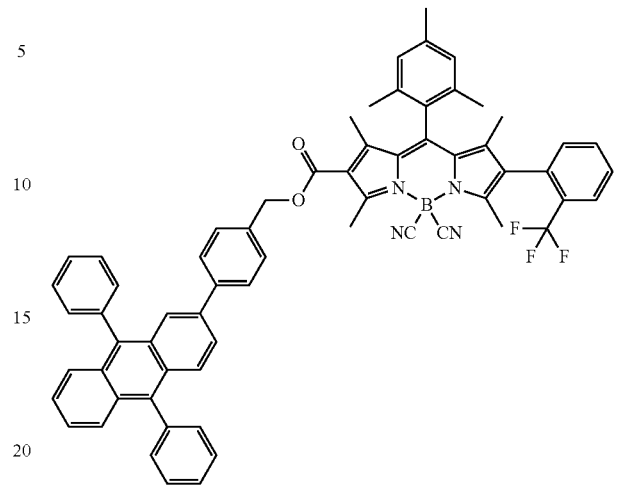
Chemical Formula 1-34
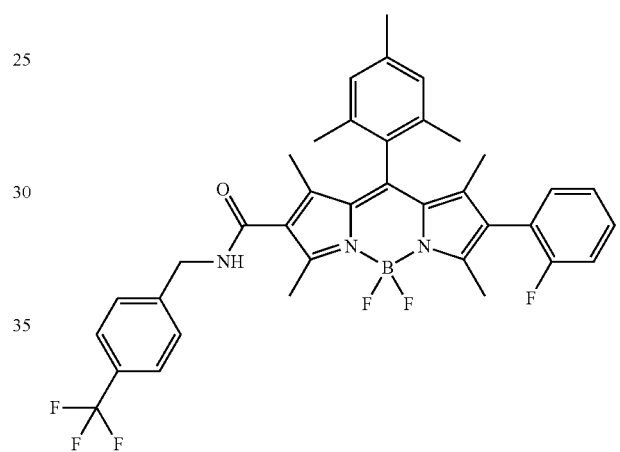
Chemical Formula 1-35
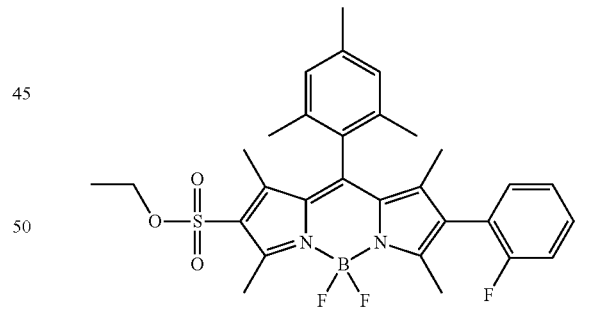
Chemical Formula 1-36
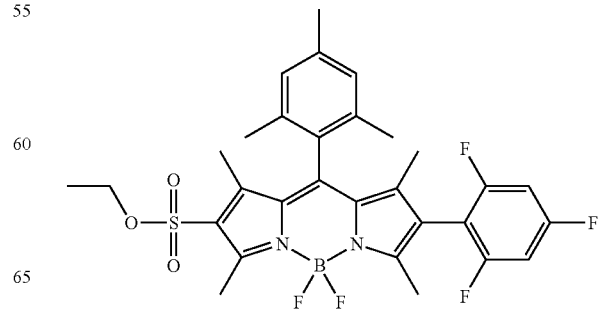

Chemical Formula 1-37
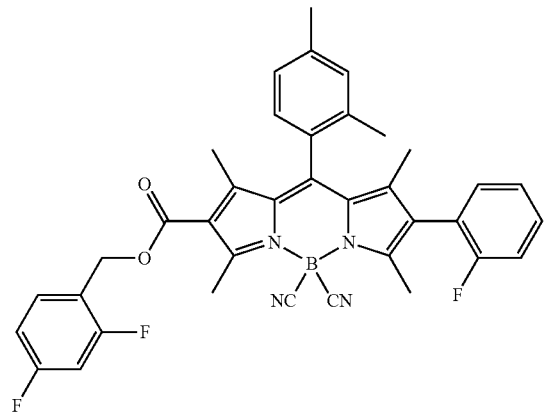
Chemical Formula 1-38
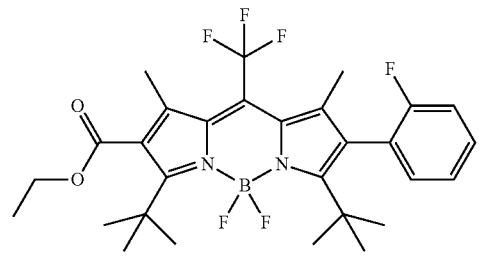
Chemical Formula 1-39
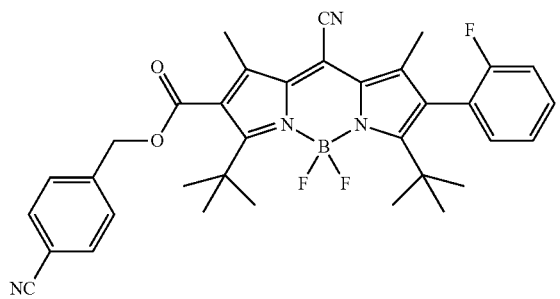
Chemical Formula 1-40
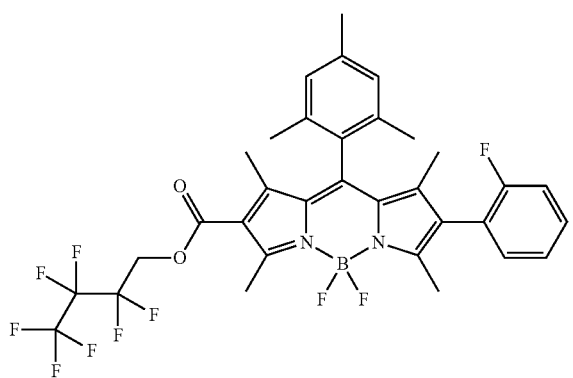
Chemical Formula 1-41
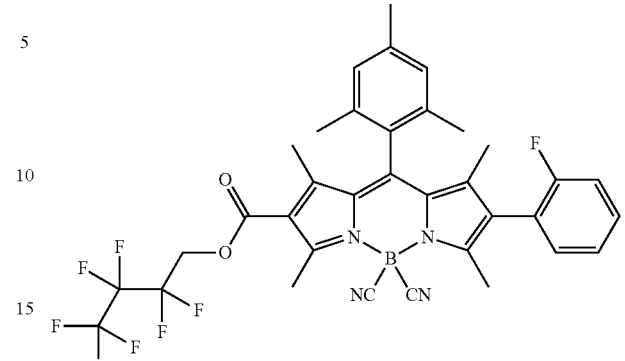
Chemical Formula 1-42
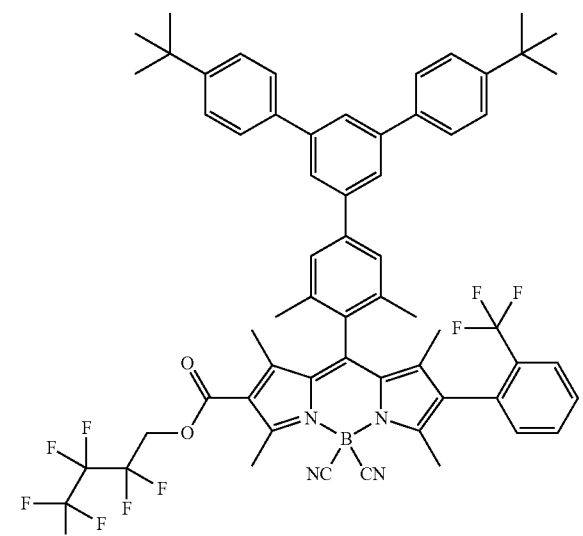
Chemical Formula 1-43
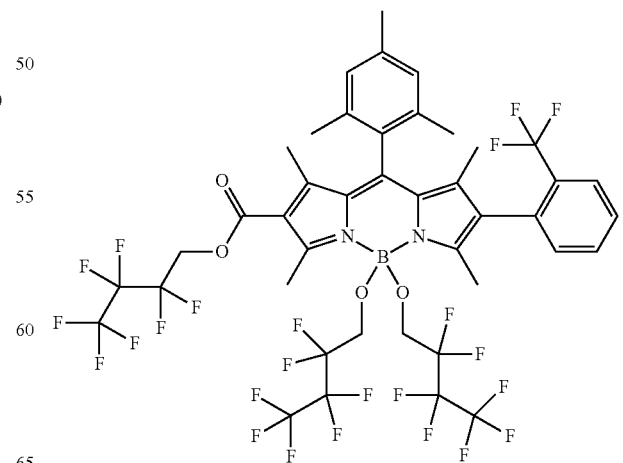

Chemical Formula 1-44
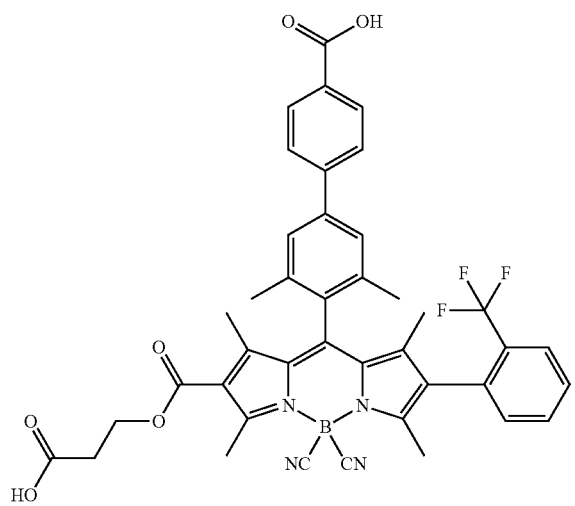
Chemical Formula 1-45
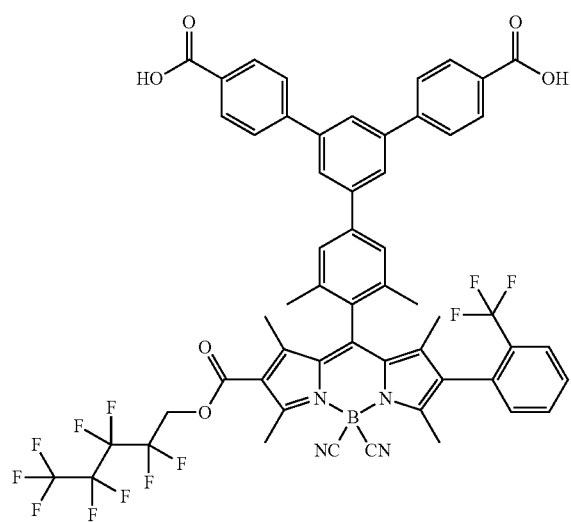
Chemical Formula 1-46
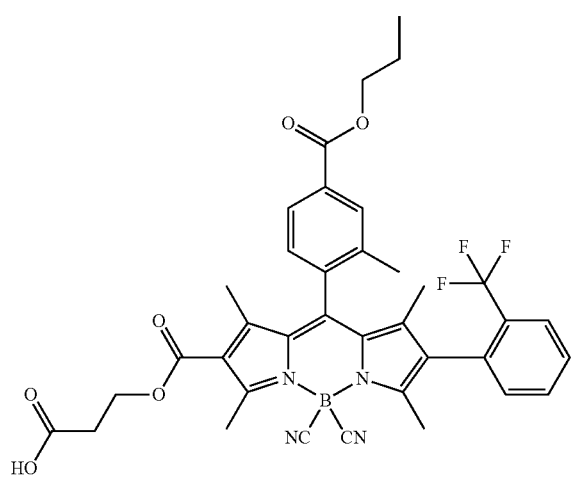
Chemical Formula 47
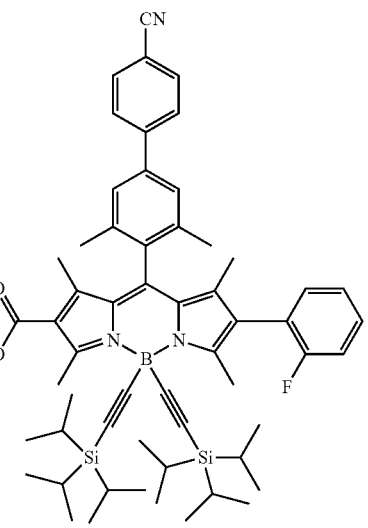
Chemical Formula 1-48
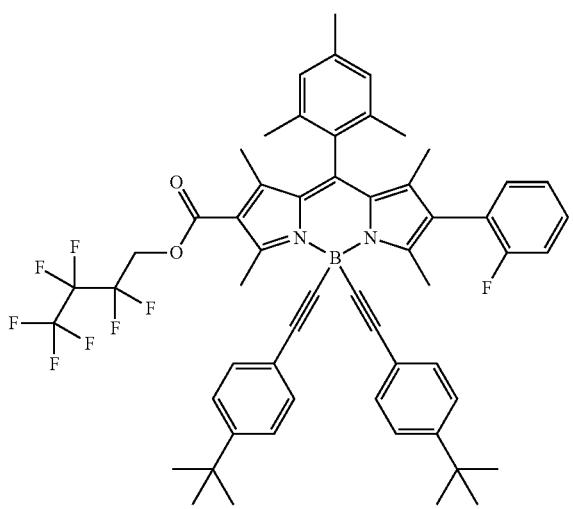
Chemical Formula 1-49
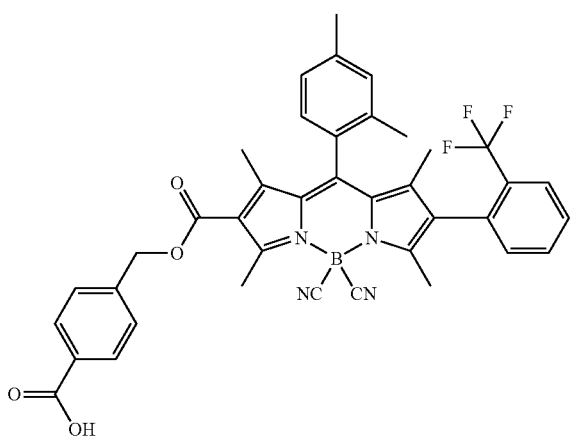

-continued
Chemical Formula 1-50
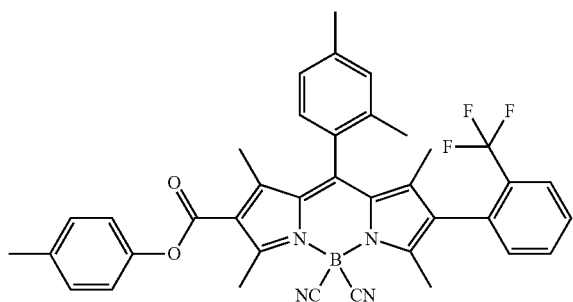
Chemical Formula 1-51
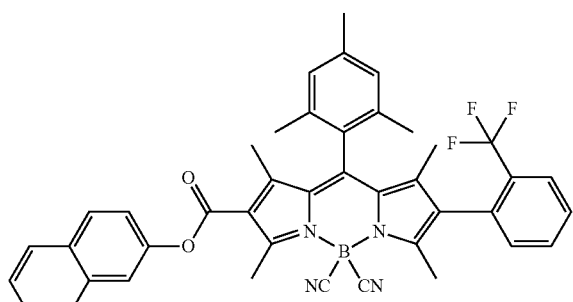
Chemical Formula 1-52
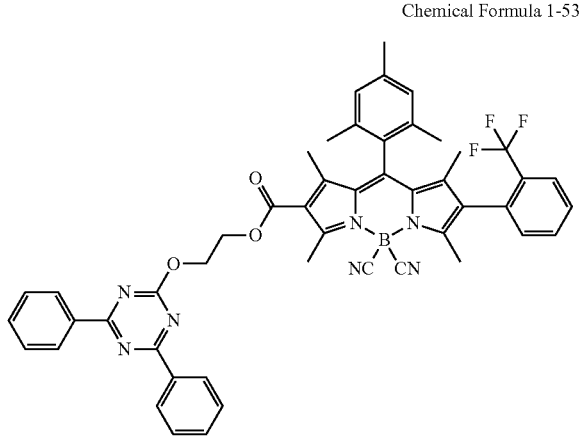
Chemical Formula 1-53
-continued
Chemical Formula 1-54
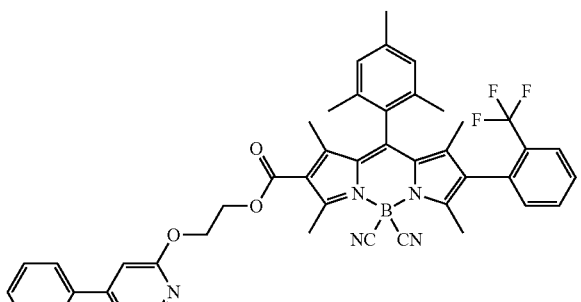
Chemical Formula 1-55
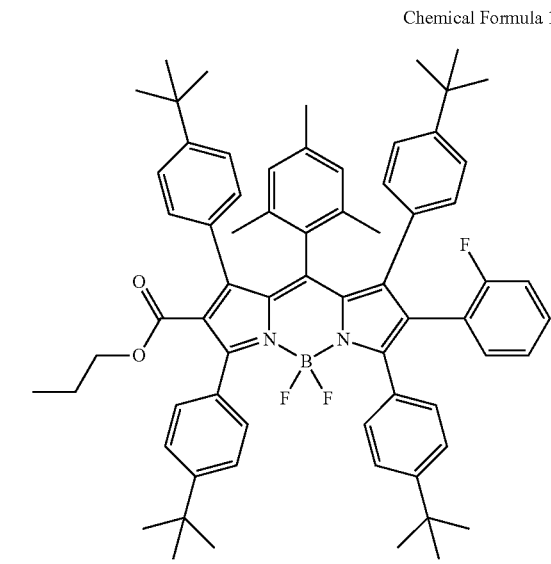
Chemical Formula 1-56
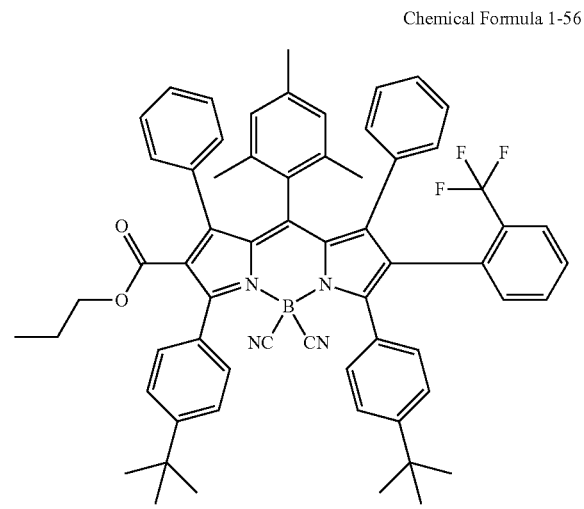

Chemical Formula 1-57
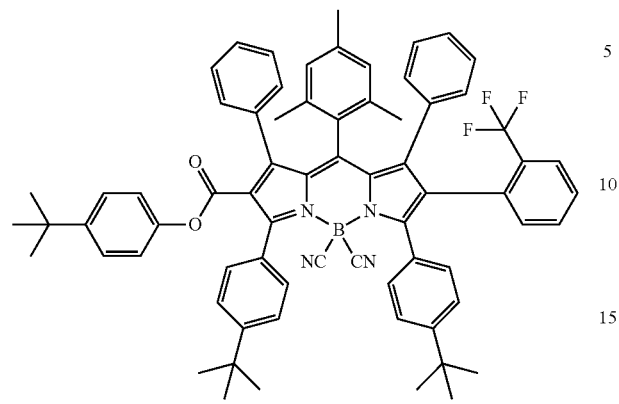
Chemical Formula 1-60
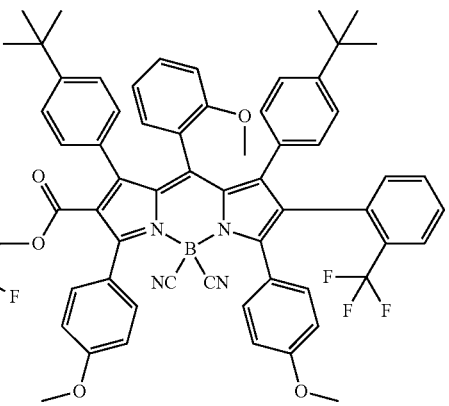
Chemical Formula 1-58
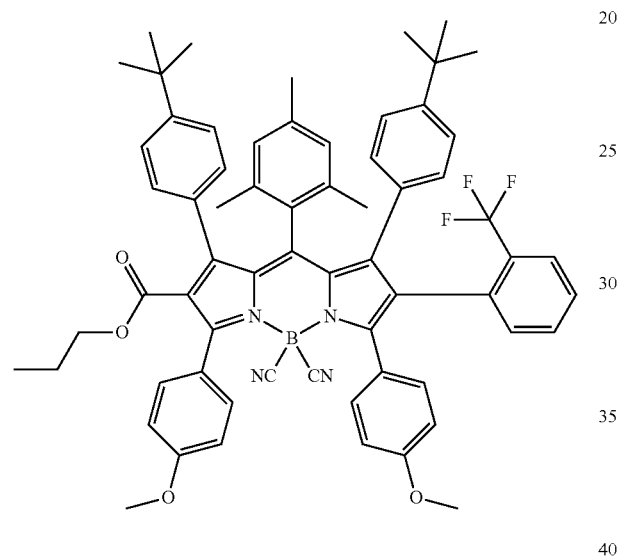
Chemical Formula 1-61
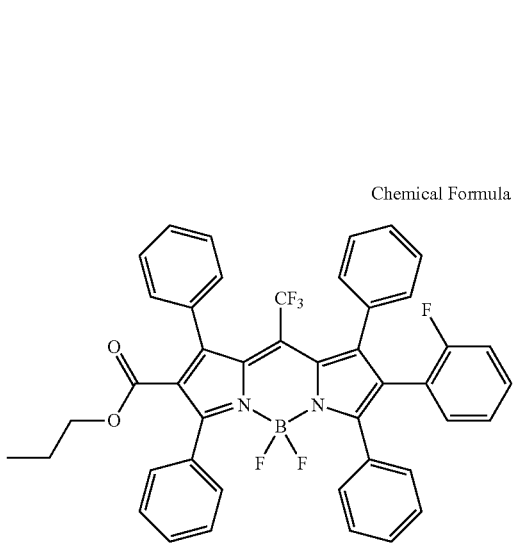
Chemical Formula 1-59
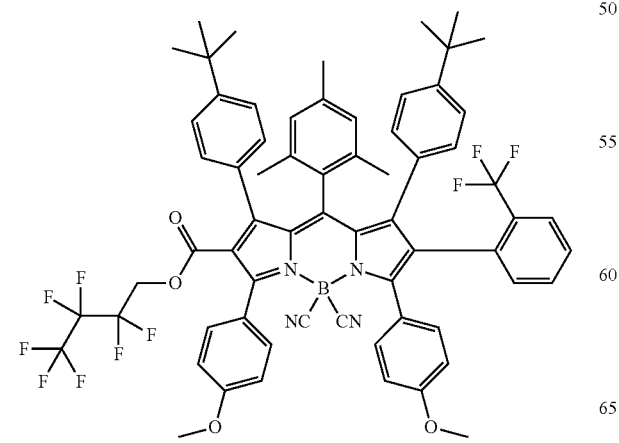
Chemical Formula 1-62
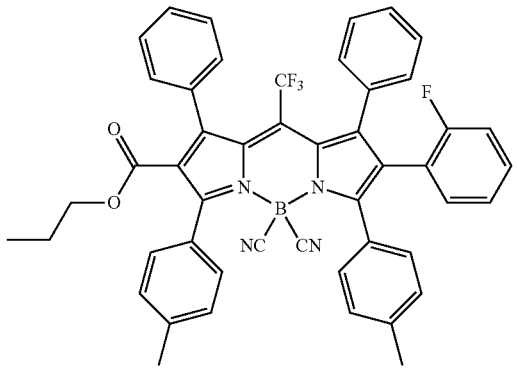

Chemical Formula 1-63
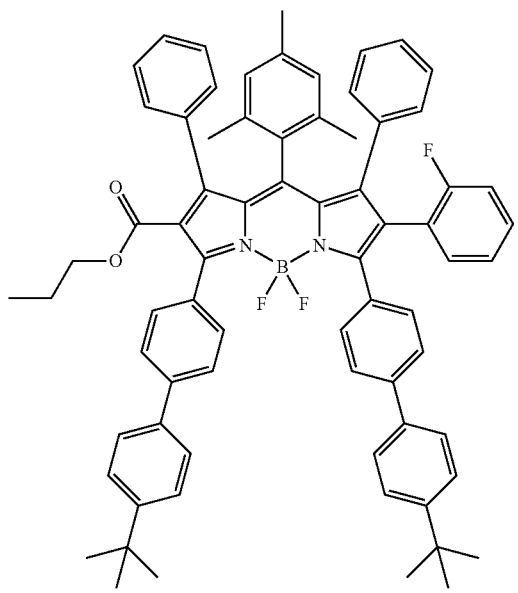
Chemical Formula 1-64
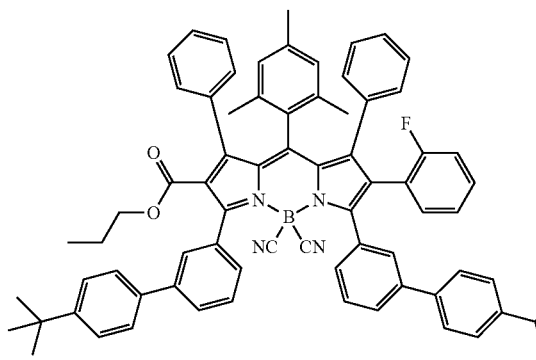
Chemical Formula 1-65
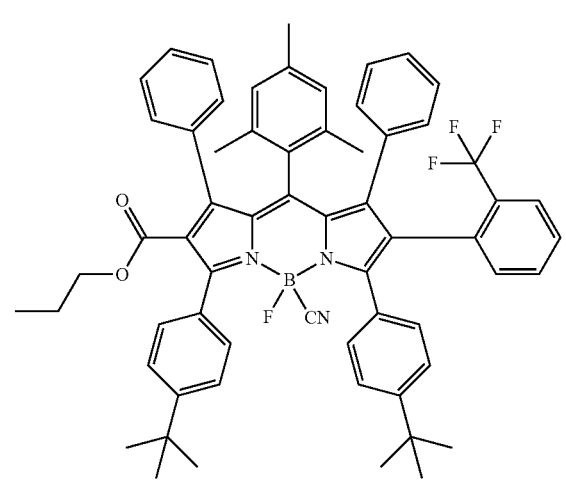
Chemical Formula 1-66
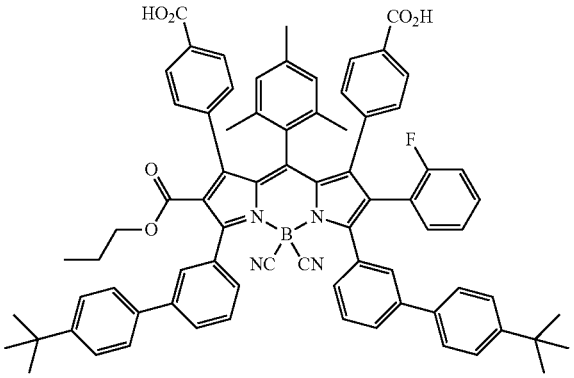
Chemical Formula 1-67
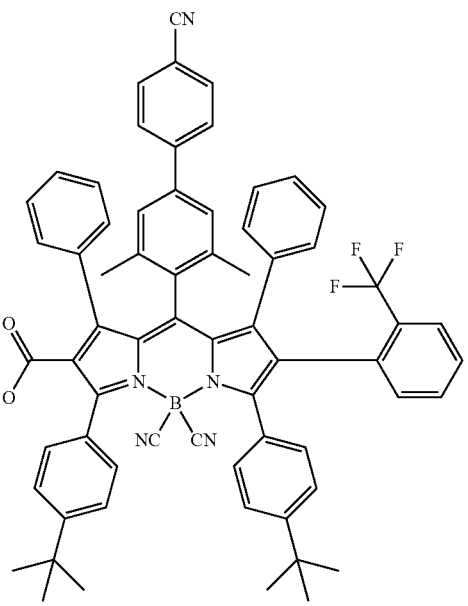
Chemical Formula 1-68
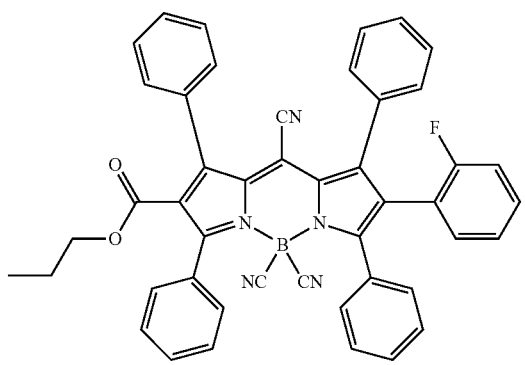

Chemical Formula 1-69

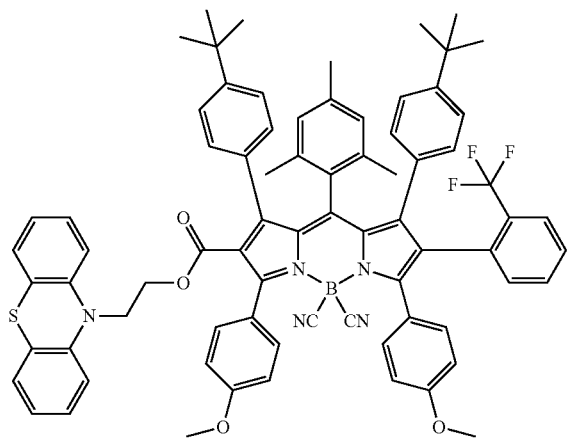

Chemical Formula 1-70

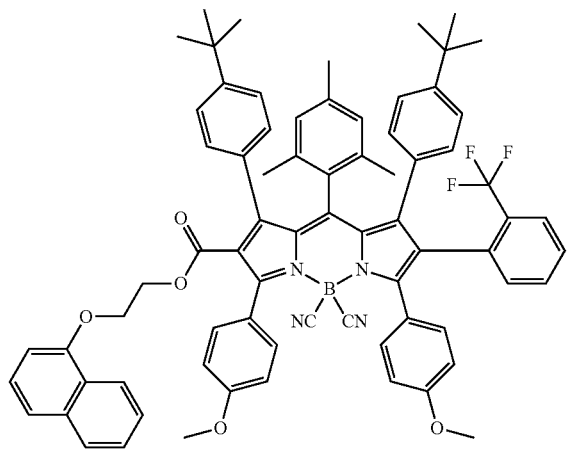

Chemical Formula 1-71

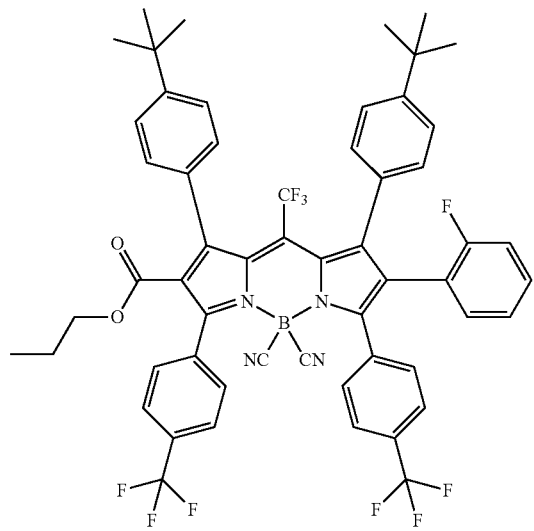

Chemical Formula 1-72

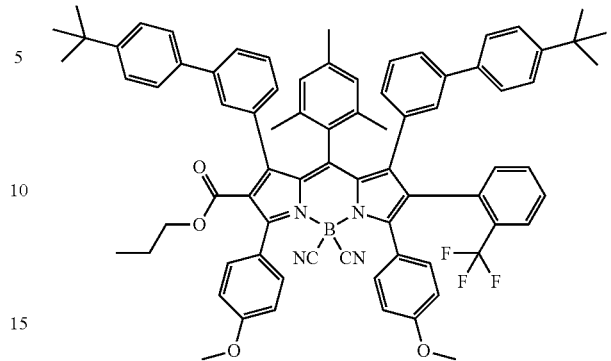

Another embodiment of the present application provides a color conversion film including a resin matrix; and the compound of Chemical Formula 1 dispersed into the resin matrix.

Content of the compound of Chemical Formula 1 in the color conversion film may be in a range of 0.001 wt % to 10 wt %.

The color conversion film may include one type of the compound of Chemical Formula 1, or two or more types thereof. For example, the color conversion film may include one type of the compound emitting green color among the compounds of Chemical Formula 1. As another example, the color conversion film may include one type of the compound emitting red color among the compounds of Chemical Formula 1. As still another example, the color conversion film may include one type of the compound emitting green color and one type of the compound emitting red color among the compounds of Chemical Formula 1.

The color conversion film may further include additional fluorescent materials in addition to the compound of Chemical Formula 1. When using a light source emitting blue light, the color conversion film preferably includes both a green light emitting fluorescent material and a red light emitting fluorescent material. In addition, when using a light source emitting blue light and green light, the color conversion film may include only a red light emitting fluorescent material. However, the case is not limited thereto, and even when using a light source emitting blue light, the color conversion film may include only a red light emitting compound when laminating a separate film including a green light emitting fluorescent material. On the other hand, even when using a light source emitting blue light, the color conversion film may include only a green light emitting compound when laminating a separate film including a red light emitting fluorescent material.

The color conversion film may further include an additional layer including a resin matrix; and a compound dispersed into the resin matrix and emitting light having a wavelength different from the compound of Chemical Formula 1. The compound emitting light having a wavelength different from the compound of Chemical Formula 1 may also be a compound represented by Chemical Formula 1, or may be a different known fluorescent material.

Materials of the resin matrix are preferably a thermoplastic polymer or a thermocuring polymer. Specifically, poly(meth)acryl series such as polymethyl methacrylate (PMMA), polycarbonate series (PC), polystyrene series (PS), polyarylene series (PAR), polyurethane series (TPU), styrene-acrylonitrile series (SAN), polyvinylidene fluoride series (PVDF), modified polyvinylidene fluoride series (modified-PVDF) and the like may be used as materials of the resin matrix.

According to another embodiment of the present application, the color conversion film according to the embodiments described above further includes light diffusion particles. By dispersing light diffusion particles into the color conversion film to enhance luminance instead of a light diffusion film used in the art, an attaching process may not be included and higher luminance may be obtained as well compared to cases using a separate light diffusion film.

As the light diffusion particles, particles having a high refractive index with the resin matrix may be used, and examples thereof include $TiO_2$, silica, borosilicate, alumina, sapphire, air or other gases, air- or gas-filled porous beads or particles (for example, air/gas-filled glass or polymer); polystyrene, polycarbonate, polymethyl methacrylate, acryl, methyl methacrylate, styrene, a melamine resin, a formaldehyde resin, or polymer particles including melamine and formaldehyde resins, or any suitable combination thereof.

Particle diameters of the light diffusion particles are in a range of 0.1 micrometers to 5 micrometers, for example, in a range of 0.3 micrometers to 1 micrometer. Content of the light diffusion particles may be determined as necessary, and for example, may be in a range of approximately 1 to 30 parts by weight based on 100 parts by weight of the resin matrix.

The color conversion film according to the embodiments described above may have a thickness of 2 micrometers to 200 micrometers. Particularly, the color conversion film is capable of exhibiting high luminance even with a small thickness of 2 micrometers to 20 micrometers. This is due to the fact that the content of the fluorescent material molecules included in the unit volume is higher than the content of quantum dots.

The color conversion film according to the embodiments described above may be provided with a substrate on one surface. This substrate may function as a support when preparing the color conversion film. The type of the substrate is not particularly limited, and materials and thicknesses thereof are not limited as long as the substrate is transparent and capable of functioning as a support. Herein, being transparent means visible ray transmissivity of 70% or more. For example, a PET film may be used as the substrate.

The color conversion film described above may be prepared by coating a resin solution dissolving the compound of Chemical Formula 1 described above on a substrate and drying the result, or extruding the compound of Chemical Formula 1 described above with a resin, and filming the result.

The compound of Chemical Formula 1 described above is dissolved in the resin solution, and therefore, the compound of Chemical Formula 1 is uniformly distributed in the solution. This is different from a quantum dot film preparation process requiring a separate dispersion process.

The resin solution dissolving the compound of Chemical Formula 1 is not particularly limited in the preparation method as long as the compound of Chemical Formula 1 described above is dissolved in the resin solution.

According to one example, the resin solution dissolving the compound of Chemical Formula 1 may be prepared using a method of preparing a first solution by dissolving the compound of Chemical Formula 1 in a solvent, preparing a second solution by dissolving a resin in a solvent, and mixing the first solution and the second solution. When the first solution and the second solution are mixed, these preferably are homogeneously mixed. However, the method is not limited thereto, and a method of adding and dissolving the compound of Chemical Formula 1 and a resin in a solvent at the same time, a method of dissolving the compound of Chemical Formula 1 in a solvent and then adding and dissolving a resin thereto, a method of dissolving a resin in a solvent and then adding and dissolving the compound of Chemical Formula 1 thereto, and the like, may be used.

As the resin included in the solution, the resin matrix material described above, a monomer capable of being cured using this resin matrix, or a mixture thereof, may be used. For example, the monomer capable of being cured using this resin matrix includes a (meth)acryl-based monomer, and this may be formed to a resin matrix material through UV curing. When using such a curable monomer, an initiator required for the curing may be further added as necessary.

The solvent is not particularly limited as long as the solvent is capable of being removed by drying afterwords without exercising a bad influence on the coating process. Nonlimiting examples of the solvent include toluene, xylene, acetone, chloroform, various alcohol-based solvents, methylethyl ketone (MEK), methylisobutyl ketone (MIBK), ethyl acetate (EA), butyl acetate, dimethylformamide (DMF), dimethylacetamide (DMAc), dimethyl sulfoxide (DMSO), N-methyl-pyrrolidone (NMP) and the like, and one type, or a mixture of two or more types may be used. When the first solution and the second solution are used, solvents included in each of the solutions may be the same as or different from each other. Even when different types of solvents are used in the first solution and the second solution, these solvents preferably have compatibility so as to be mixed to each other.

The process of coating the resin solution dissolving the compound of Chemical Formula 1 on a substrate may use a roll-to-roll process. For example, a process of unwinding a substrate from a substrate-wound roll, coating the resin solution dissolving the compound of Chemical Formula 1 on one surface of the substrate, drying the result, and then winding the result again on a roll may be used. When using a roll-to-roll process, viscosity of the resin solution is preferably determined within a range capable of carrying out the above-mentioned process, and for example, the viscosity may be determined within a range of 200 cps to 2,000 cps.

As the coating method, various known methods may be used, and for example, a die coater may be used, or various bar coating methods such as a comma coater and a reverse comma coater may be used.

After the coating, a drying process is carried out. The drying process may be carried out under a condition required for removing the solvent. For example, a color conversion film including a fluorescent material including the compound of Chemical Formula 1 having a target thickness and concentration may be obtained on a substrate by carrying out drying under a condition sufficiently removing a solvent in an oven placed adjacent to a coater in a direction of a substrate progressing during a coating process.

When a monomer that is capable of being cured with the resin matrix resin is used as a resin included in the solution, curing, for example, UV curing, may be carried out prior to or at the same time with the drying.

When filming the compound of Chemical Formula 1 with a resin through extrusion, extrusion methods known in the art may be used, and for example, a color conversion film may be prepared by extruding the compound of Chemical Formula 1 with a resin such as polycarbonate series (PC), poly(meth)acryl series and styrene-acrylonitrile series (SAN).

According to another embodiment of the present application, the color conversion film may be provided with a protective film or a barrier film on at least one surface. As the protective film and the barrier film, those known in the art may be used.

Another embodiment of the present application provides a backlight unit including the color conversion film described above. The backlight unit may have a backlight unit constitution known in the art except that it includes the color conversion film described above. FIG. 1 shows a mimetic view of a backlight unit structure according to one example. The backlight unit according to FIG. 1 includes a side chain-type light source (blue color), a reflective plate surrounding the light source (green color), a light guide plate (apricot color) directly emitting light from the light source, or inducing light reflected from the reflective plate, a reflective layer (sky blue color) provided on one surface of the light guide plate, and a color conversion film (white color) provided on the opposite surface of a surface facing the reflective layer of the light guide plate. However, the scope of the present invention is not limited to FIG. 1, and the light source may use a direct type as well as a side chain type, and the reflective plate or the reflective layer may not be included or may be replaced with other constitutions, and as necessary, additional films such as a light diffusion film, a light collecting film, a luminance enhancing film and the like may be further provided.

Another embodiment of the present application provides a display device including the backlight unit. The display device is not particularly limited as long as it includes the backlight unit, and may be included in TVs, computer monitors, laptops, mobile phones and the like.

Hereinafter, the present invention will be described with reference to examples. However, the examples below are for illustrative purposes only, and the scope of the present invention is not limited thereto.

REFERENCE EXAMPLES 1 TO 3

In order to examine spectroscopic properties and light stability of the following Compounds 1 to 3 and 1-40, light emission spectra in a solution state (toluene $1\times10^{-5}$ M) were measured, and stability of the molecules themselves for light was evaluated through absorbance differences by time by measuring UV-vis spectra under a blue backlight.

화합물 1

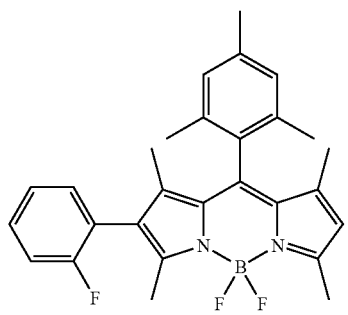

-continued

화합물 2

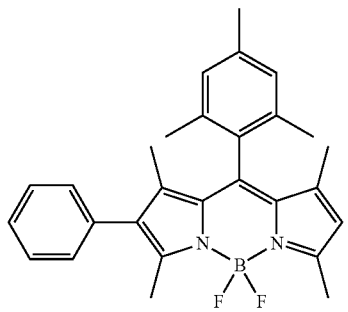

화합물 3

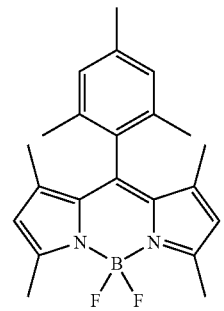

화합물 1-40

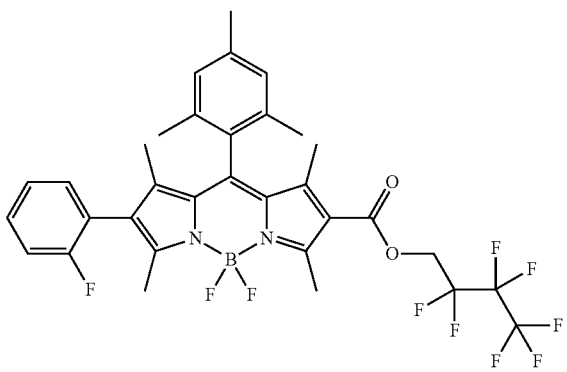

FIG. 2 shows light emission spectra (toluene $1\times10^{-5}$ M) of Compound 1 (dotted line) and Compound 2 (straight line). As shown in FIG. 2, it was identified that, when ortho-fluorophenyl substitutes, the light emission wavelength was suitable for green compared to Compound 2, and the half-width significantly decreased.

FIG. 3 and FIG. 4 each show changes in the UV-vis spectra of Compound 1 and Compound 3 by time under blue light. FIG. 5 shows absorbance variation in the maximum absorption wavelengths of Compound 1 (■) and Compound 3 (♦) by time (toluene $1\times10^{-5}$ M). It was seen that Compound 1 substituted with ortho-fluorophenyl had smaller changes in the absorbance by time compared to Compound 3 that was not substituted. This supports the fact that light stability is significantly enhanced when introducing an ortho-fluorophenyl group.

FIG. 6 shows changes in the UV-vis spectra of Compound 1-40 by time under blue light. FIG. 7 shows absorbance variation in the maximum absorption wavelengths of Compound 1 (■) and Compound 1-40 (●) (toluene $1\times10^{-5}$ M). Compound 1-40 additionally introducing an ester group to ortho-fluorophenyl-substituted Compound 1 had almost no changes in the absorbance by time under a blue light source. Accordingly, the structure of Chemical Formula 1 introducing an ortho-fluorophenyl group and an electron withdrawing group at the same time may play a role of a green fluorescent substance with significantly enhanced light stability. When a color conversion film using such compounds is used for display materials, Color Gamut and efficiency may increase, and durability may be significantly enhanced.

SYNTHESIS EXAMPLE 1

Preparation of Compound 1-9

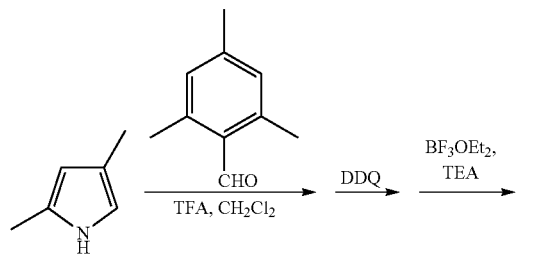

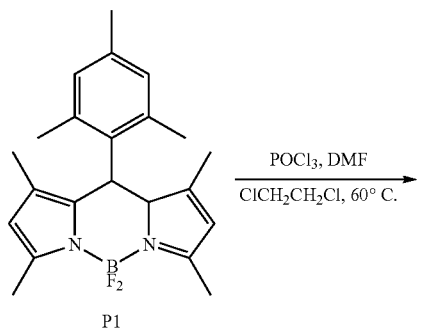

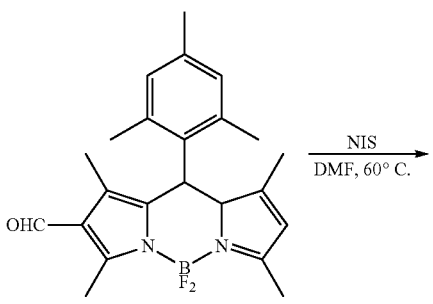

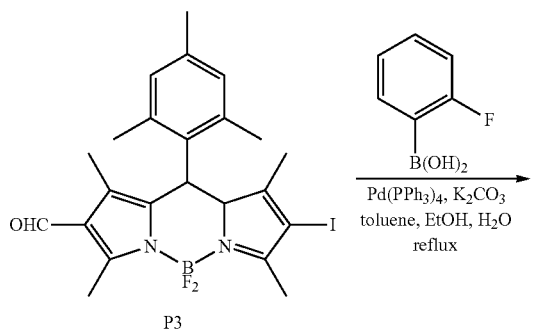

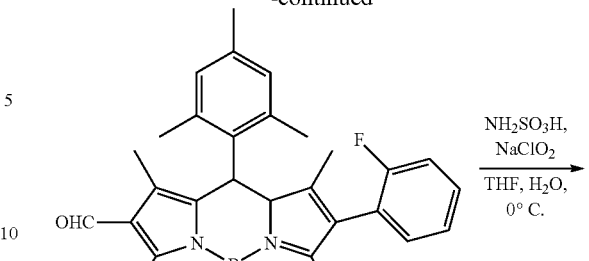

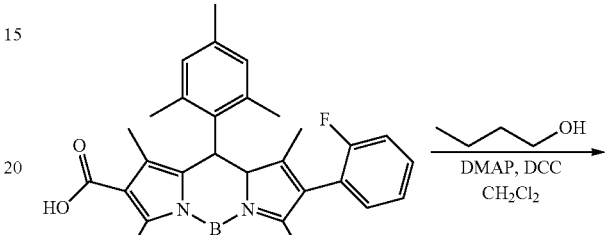

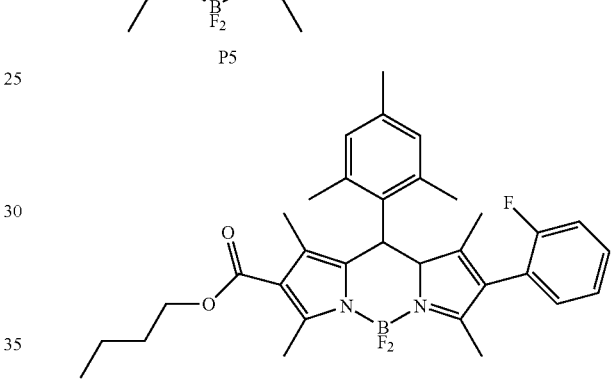

Preparation of Compound P1: After mixing 2,4-dimethylpyrrole (10 g, 0.10 mol), mesityl aldehyde (7.8 g, 0.052 mol), trifluoroacetic acid (2 drops), and dry dichloromethane (500 mL) in a flask, the result was stirred for 5 hours at room temperature under nitrogen. After checking the disappearance of the starting materials using TLC, DDQ (12 g, 0.052 mol) was added thereto at 0° C. The result was stirred for 1 hour at room temperature, and then triethylamine (26 g, 0.25 mol) was slowly added dropwise thereto. After the result was stirred for 30 minutes at room temperature, a boron trifluoride ethyl ether complex (65 g, 0.46 mol) was slowly added dropwise thereto. The reactants were stirred for 5 hours at room temperature, water was added thereto, and the result was extracted using dichloromethane. The result was dried with anhydrous magnesium sulfate and filtered, and then vacuum distilled to remove the solvent. A red compound P1 (7.8 g, 40%) was obtained through a silica-gel column (hexane/ethyl acetate).

$[M-F]^+=347$

Preparation of Compound P2: After mixing dimethylformamide (4 mL) and dichloroethane (50 mL) in a flask, the temperature was lowered to 0° C. Under nitrogen atmosphere, $POCl_3$ (4 mL) was slowly added dropwise thereto, and the result was stirred for 30 minutes at room temperature. After adding Compound P1 (3 g, 8.2 mmol) to the reaction solution, the result was warmed to 60° C. and then stirred for 1 hour. The result was cooled to room temperature and added to a mixed solution of ice and a saturated aqueous sodium hydroxide solution. The result was stirred for 2 hours at room temperature, and extracted with chloroform. The result was dried with anhydrous magnesium sulfate and filtered, and then vacuum distilled to remove the solvent. Red solid Compound P2 (2.9 g, 89%) was obtained through a silica-gel column (hexane/ethyl acetate).

$[M-F]^+=375$

Preparation of Compound P3: After dissolving Compound P2 (2.1 g, 5.3 mmol) and N-iodosuccinimide (3.6 g, 16 mmol) in DMF in a flask, the result was stirred for 5 hours at 60° C. After the result was cooled to room temperature, water was added thereto to filter solid. The solid was dissolved in $CHCl_3$, and washed with a saturated $Na_2S_2O_3$ solution. The result was dried with anhydrous magnesium sulfate and then silica filtered. The result was vacuum distilled to remove the solvent, and dark red Compound P3 (2.3 g, 83%) was obtained through a silica column (hexane/ethyl acetate).

$[M-F]^+=501$

Preparation of Compound P4: After dissolving Compound P3 (2.0 g, 3.8 mmol) and 1-fluorophenylboronic acid (0.61 g, 4.3 mmol) in toluene and ethanol, potassium carbonate ($K_2CO_3$, 1.6 g, 11.5 mmol) and water were added to the reaction solution, and then tetrakis(triphenylphosphine)palladium (0.2 g, 0.16 mmol) was added thereto. The result was stirred under reflux for 5 hours and cooled to room temperature, and then extracted with chloroform. The result was dried with anhydrous magnesium sulfate and filtered, and then vacuum distilled to remove the solvent. Dark red solid P4 (1.8 g, 94%) was obtained through a silica-gel column.

$[M-F]^+=469$

Preparation of Compound P5: After dissolving Compound P4 (0.60 g, 1.2 mmol) and $NH_2SO_3H$ (0.12 g, 1.2 mol) in tetrahydrofuran, $NaCl_2$ (0.11 g, 1.2 mmol) dissolved in water was slowly added dropwise thereto at 0° C. The result was stirred for 1 hour at room temperature, a saturated $Na_2S_2O_3$ solution was added thereto, and the result was extracted with chloroform. The result was dried with anhydrous magnesium sulfate and filtered, and then vacuum distilled to remove the solvent, and red Compound P5 (0.59 g, 91%) was obtained.

$[M-F]^+=485$

Preparation of Compound 1-9: After dissolving Compound P5 (0.50 g, 0.99 mmol), n-butanol (0.1 g, 1.3 mmol) and DMAP (10 mg, 0.08 mmol) in dichloromethane, DCC (0.22 g, 1.0 mmol) dissolved in dichloromethane was slowly added dropwise thereto at 0° C. The result was stirred for 12 hours at room temperature, a saturated sodium hydroxide solution was added thereto, and the result was extracted with chloroform. The result was dried with anhydrous magnesium sulfate and filtered, and then vacuum distilled to remove the solvent. Orange solid Compound 1-9 (0.43 g, 76%) was obtained through a silica-gel column.

$[M-F]^+=541$

SYNTHESIS EXAMPLE 2

Preparation of Compound 1-40

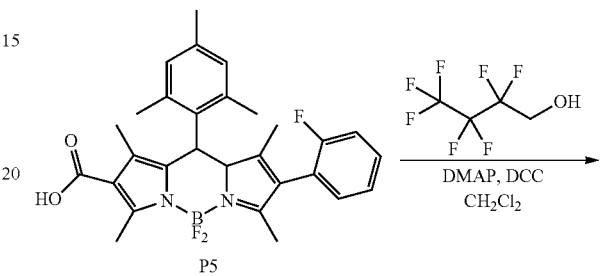

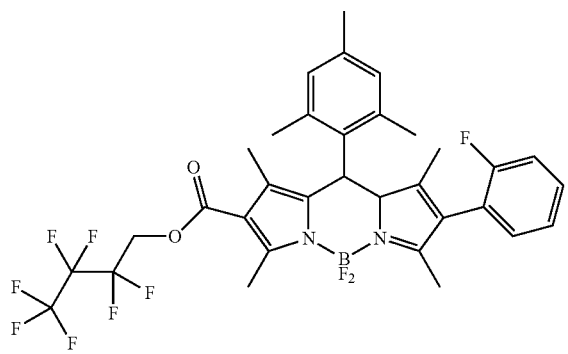

Orange Compound 1-40 (0.43 g, 52%) was obtained in the same manner as in Synthesis Example 1 except that 2,2,3,3,4,4-heptafluorobutanol (0.31 g, 1.5 mmol) was used instead of n-butanol.

$[M-F]^+=667$

SYNTHESIS EXAMPLE 3
Preparation of Compound 1-41
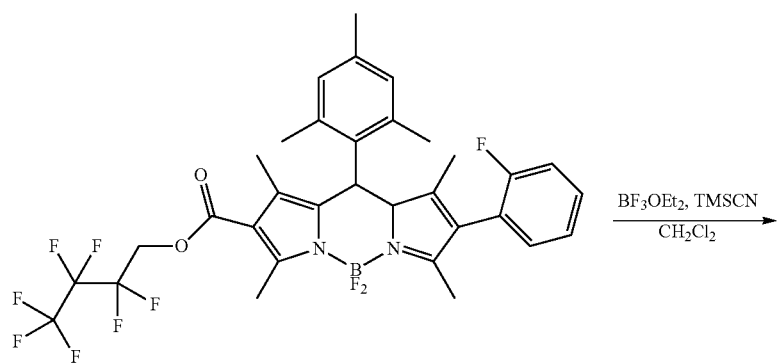
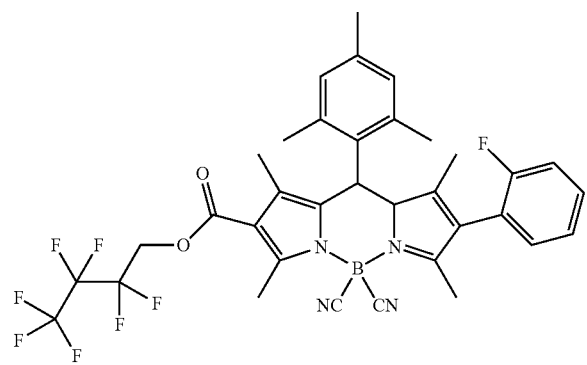

After dissolving Compound 1-40 (0.50 g, 0.72 mmol) in dichloromethane, a boron trifluoride ethyl ether complex (0.31 g, 2.18 mmol) was slowly added dropwise thereto at 0° C. The result was stirred for 3 hours at room temperature, and then TMSCN (0.43 g, 4.3 mmol) was added dropwise thereto. The result was stirred for 5 hours at room temperature, a saturated NaHCO$_3$ solution was added thereto, and the result was extracted with chloroform. The result was dried with anhydrous magnesium sulfate and filtered, and then vacuum distilled to remove the solvent. Orange solid Compound 1-41 (0.46 g, 90%) was obtained through a silica-gel column.

$[M+H]^+ = 701$

SYNTHESIS EXAMPLE 4

Preparation of Compound 1-43

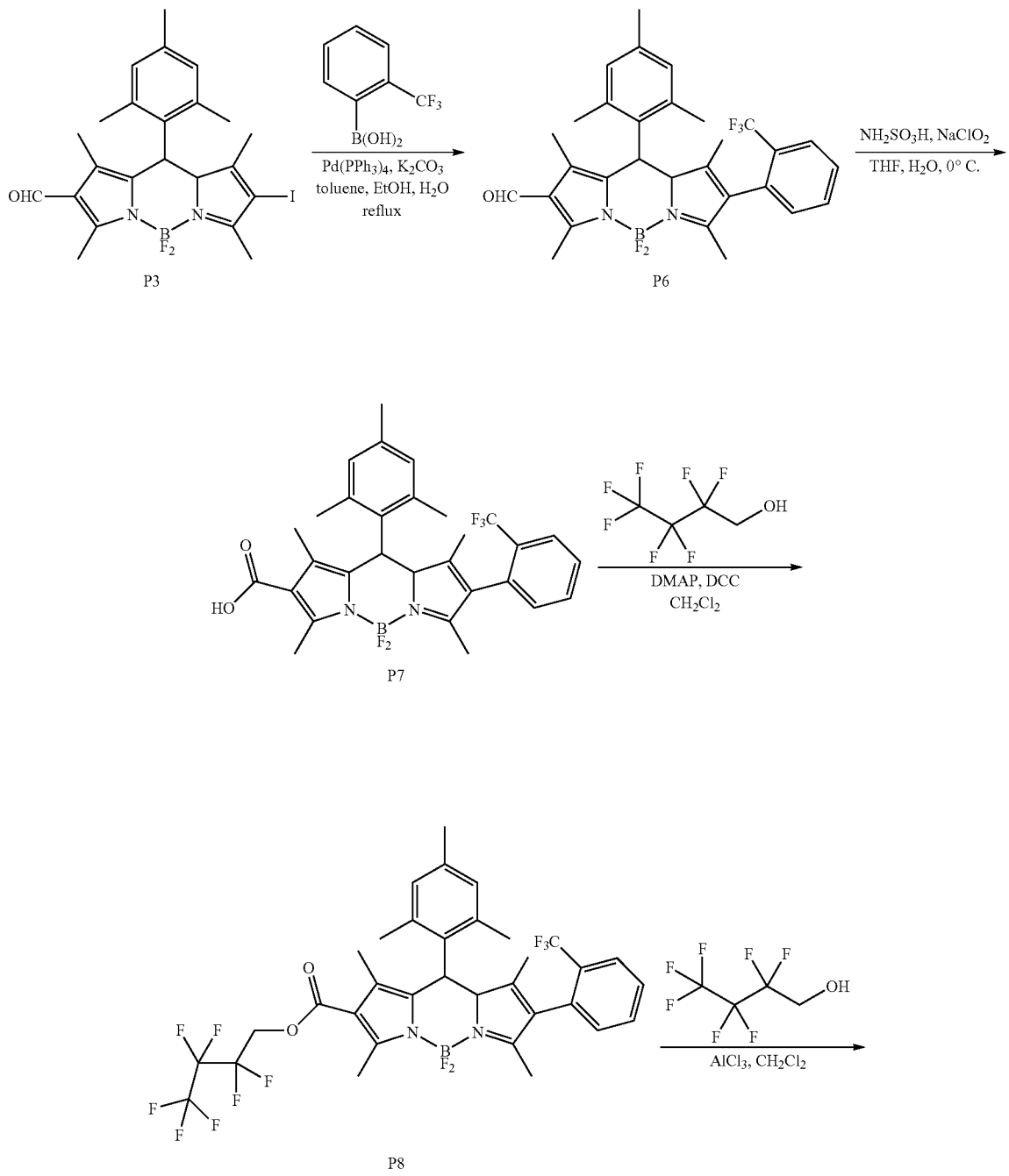

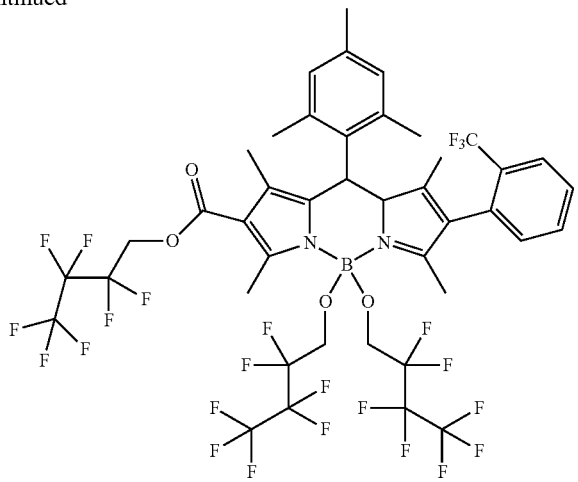

Preparation of Compound P6: Orange Compound P6 (0.51 g, 65%) was obtained in the same manner as in the preparation of Compound P4 of Synthesis Example 1, except that 2-trifluoromethyl-phenylboronic acid (0.31 g, 1.63 mmol) was used instead of fluorophenylboronic acid.

[M-F]$^+$=519

Preparation of Compound P7: Red Compound P7 (0.41 g, 77%) was obtained in the same manner as in the preparation of Compound P5 of Synthesis Example 1, except that Compound P6 (0.51 g, 0.94 mmol) was used instead of Compound P4.

[M-F]$^+$=535

Preparation of Compound P8: Orange Compound P8 (0.35 g, 71%) was obtained in the same manner as in the preparation of Compound 1-9 of Synthesis Example 1, except that 2,2,3,3,4,4-heptafluorobutanol (0.22 g, 1.09 mmol) was used instead of n-butanol.

[M-F]$^+$=717

Preparation of Compound 1-43: Under nitrogen atmosphere, Compound P8 (0.31 g, 0.42 mmol) was dissolved in dichloromethane, and then AlCl$_3$ (0.10 g, 0.75 mmol) was added thereto at 0° C. The result was stirred under reflux for 2 hours, and 2,2,3,3,4,4-heptafluorobutanol (1.01 g, 5.04 mmol) was added dropwise thereto. The result was stirred under reflux for 5 hours, cooled to room temperature, and the reaction solution was added to water. The result was extracted with dichloromethane, dried with anhydrous magnesium sulfate and filtered, and then vacuum distilled to remove the solvent. Orange solid Compound 1-43 (0.41 g, 88%) was obtained through a silica-gel column.

[M+H]$^+$=1097

EXAMPLE 1

A first solution was prepared by dissolving Compound 1-9 in DMF. A second solution was prepared by dissolving a thermoplastic resin SAN in a DMF solvent. The first solution and the second solution were mixed so that the amount of the organic fluorescent substance became 0.5 parts by weight based on 100 parts by weight of the SAN, and then uniformly mixed. Solid content of the mixed solution was 20% by weight, and the viscosity was 200 cps. A color conversion film was prepared by coating this solution on a PET substrate and drying the result. The luminance spectrum of the prepared color conversion film was measured using a spectroradiometer (SR series manufactured by TOPCON). Specifically, the prepared color conversion film was laminated on one surface of a light guide plate of a backlight unit including an LED blue backlight (maximum light emission wavelength 450 nm) and a light guide plate, then a prism sheet and a DBEF film were laminated on the color conversion film, and a luminance spectrum of the film was measured. When measuring the luminance spectrum, the initial value was set so that brightness of blue LED light became 600 nit without the color conversion film.

The color conversion film of Compound 1-9 emitted light at 547 nm under blue LED light, and a half-width was 36 nm. A ratio of the decrease in blue fluorescence to the increase in green fluorescence after laminating the color conversion film on the blue backlight was 0.97. Under the driving of the blue backlight, intensity of green fluorescence decreased by 48% after 400 hours under the condition of a temperature of 60° C. and 90% RH (FIG. 8).

EXAMPLE 2

A color conversion film was prepared using Compound 1-40 according to the method of Example 1. The color conversion film of the compound emitted light at 546 nm under blue LED light, and a half-width was 36 nm. A ratio of the decrease in blue fluorescence to the increase in green fluorescence after laminating the color conversion film on the blue backlight was 0.99. Under the driving of the blue backlight, intensity of green fluorescence decreased by 22% after 400 hours under the condition of a temperature of 60° C. and 90% RH (FIG. 8).

EXAMPLE 3

A color conversion film was prepared using Compound 1-41 according to the method of Example 1. The color conversion film of the compound emitted light at 545 nm under blue LED light, and a half-width was 36 nm. A ratio of the decrease in blue fluorescence to the increase in green fluorescence after laminating the color conversion film on the blue backlight, intensity of green fluorescence decreased by 23% after 400 hours under the condition of a temperature of 60° C. and 90% RH (FIG. 8).

EXAMPLE 4

A color conversion film was prepared using Compound 1-43 according to the method of Example 1. The color conversion film of the compound emitted light at 539 nm under blue LED light, and a half-width was 35 nm. A ratio of the decrease in blue fluorescence to the increase in green fluorescence after laminating the color conversion film on the blue backlight was 0.97. Under the driving of the blue backlight, intensity of green fluorescence decreased by 32% after 400 hours under the condition of a temperature of 60° C. and 90% RH (FIG. 8).

COMPARATIVE EXAMPLE 1

A color conversion film was prepared using Compound 1 according to the method of Example 1. The color conversion film of the compound emitted light at 540 nm under blue LED light, and a half-width was 40 nm. A ratio of the decrease in blue fluorescence to the increase in green fluorescence after laminating the color conversion film on the blue backlight was 0.96. Under the driving of the blue backlight, intensity of green fluorescence decreased to 50% or less after 70 hours under the condition of a temperature of 60° C. and 90% RH (FIG. 8).

COMPARATIVE EXAMPLE 2

A color conversion film was prepared using Compound 3 according to the method of Example 1. The color conversion film of the compound emitted light at 535 nm under blue LED light, and a half-width was 41 nm. A ratio of the decrease in blue fluorescence to the increase in green fluorescence after laminating the color conversion film on the blue backlight was 0.95. Under the driving of the blue backlight, intensity of green fluorescence decreased to 50% or less after 70 hours under the condition of a temperature of 60° C. and 90% RH (FIG. 8).

As seen from the above-mentioned examples, the compound of the present invention has a smaller half-width compared to existing compounds, and may be used in the preparation of a color conversion film having enhanced light stability.

REFERENCE NUMERAL

101: Side-Chain Type Light Source
102: Reflective Plate
103: Light Guide Plate
104: Reflective Layer
105: Color Conversion Film
106: Light Dispersion Pattern

The invention claimed is:
1. A compound of the following Chemical Formula 1:

[Chemical Formula 1]

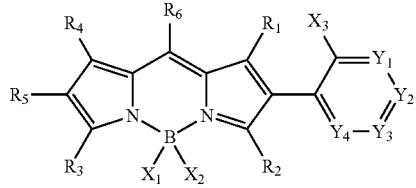

wherein, in Chemical Formula 1,
at least one of $R_1$ to $R_5$ is selected from among the following structural formulae;

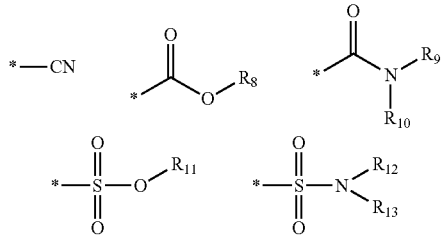

$R_6$ is hydrogen; a nitrile group; a substituted or unsubstituted alkyl group; a substituted or unsubstituted cycloalkyl group; a substituted or unsubstituted alkoxy group; a substituted or unsubstituted aryl group; a substituted or unsubstituted alkylaryl group; or a substituted or unsubstituted aromatic or aliphatic heterocyclic group;

$X_1$ and $X_2$ are the same as or different from each other, and each independently F; a nitrile group; a substituted or unsubstituted alkynyl group; a substituted or unsubstituted alkyl group; a substituted or unsubstituted alkoxy group; a substituted or unsubstituted aryloxy group; a substituted or unsubstituted arylalkoxy group; a substituted or unsubstituted aryl group; or a substituted or unsubstituted aromatic or aliphatic heterocyclic group, or bond to each other to form an aromatic or aliphatic ring;

$X_3$ is a halogen group; a nitrile group; a carbonyl group; an ester group; an amide group; a sulfonate group; a substituted or unsubstituted alkyl group; a fluoroalkyl group; a substituted or unsubstituted cycloalkyl group; a substituted or unsubstituted alkoxy group; a substituted or unsubstituted alkylsulfoxy group; a substituted or unsubstituted silyl group; a substituted or unsubstituted phosphine oxide group; or a substituted or unsubstituted alkylaryl group;

$Y_1$ is $CR_{101}$ or N, $Y_2$ is $CR_{102}$ or N, $Y_3$ is $CR_{103}$ or N and $Y_4$ is $CR_{104}$ or N; and groups of $R_1$ to $R_5$ that are not the above-mentioned structural formulae, $R_8$ to $R_{13}$ and $R_{101}$ to $R_{104}$ are the same as or different from each other, and each independently hydrogen; deuterium; a halogen group; a nitrile group; a nitro group; a carbonyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted arylalkyl group; a substituted or unsubstituted alkylaryl group; a substituted or unsubstituted aryl group; or a substituted or unsubstituted aromatic or aliphatic heterocyclic group, and $R_9$ and $R_{10}$ bond to each other to form an aliphatic or aromatic ring, and $R_{12}$ and $R_{13}$ bond to each other to form an aliphatic or aromatic ring.

2. The compound of claim 1, wherein $R_1$ to $R_4$ are the same as or different from each other, and each independently hydrogen, deuterium, a substituted or unsubstituted alkyl group, a substituted or unsubstituted alkylaryl group, a substituted or unsubstituted arylalkyl group, a substituted or unsubstituted aryl group, or one of the following structural formulae:

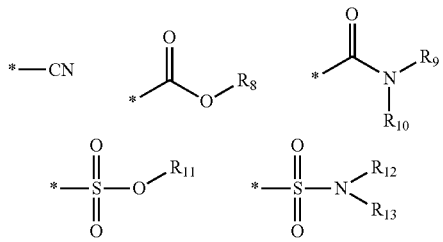

wherein definitions of $R_8$ to $R_{13}$ are the same as those described above.

3. The compound of claim 1, wherein $R_5$ is hydrogen, deuterium, or one of the following structural formulae:

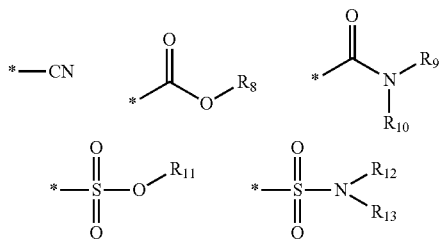

wherein definitions of $R_8$ to $R_{13}$ are the same as those described above.

4. The compound of claim 1, wherein $Y_1$ to $Y_4$ are the same as or different from each other, and each independently CH, CF or N.

5. The compound of claim 1, wherein the compound of Chemical Formula 1 has a maximum light emission peak present in 520 nm to 550 nm in a film state.

6. The compound of claim 1, wherein the compound of Chemical Formula 1 has a maximum light emission peak present in 520 nm to 550 nm in a film state, and a half-width of the light emission peak is 50 nm or less.

7. The compound of claim 1, wherein the compound of Chemical Formula 1 has a maximum light emission peak present in 610 nm to 650 nm in a film state.

8. The compound of claim 1, wherein the compound of Chemical Formula 1 has a maximum light emission peak present in 610 nm to 650 nm in a film state, and a half-width of the light emission peak is 60 nm or less.

9. The compound of claim 1, wherein the compound of Chemical Formula 1 has quantum efficiency of 0.9 or more.

10. The compound of claim 1, wherein Chemical Formula 1 is selected from among the following structural formulae:

Chemical Formula 1-1

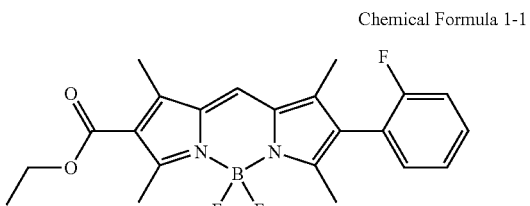

Chemical Formula 1-2

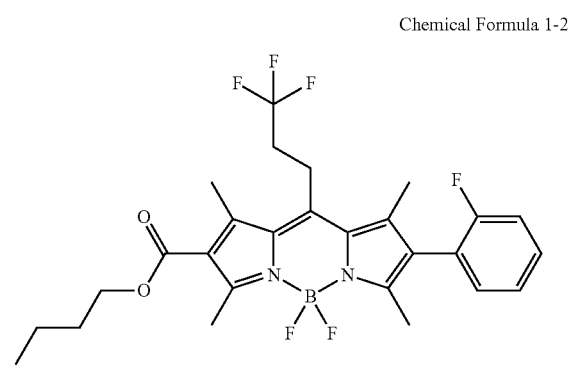

Chemical Formula 1-3

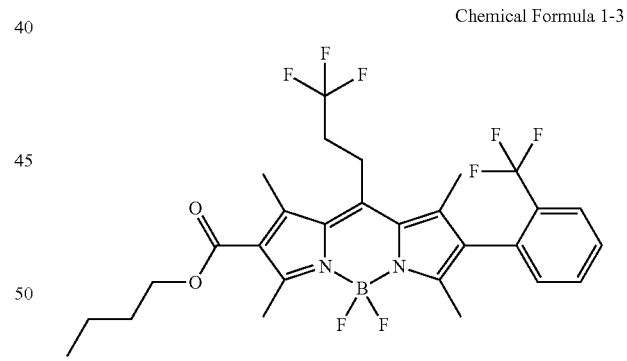

Chemical Formula 1-4

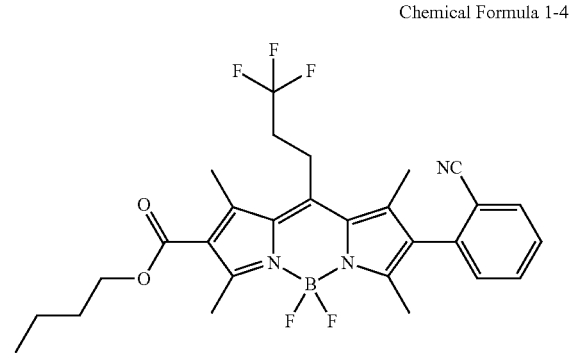

Chemical Formula 1-5
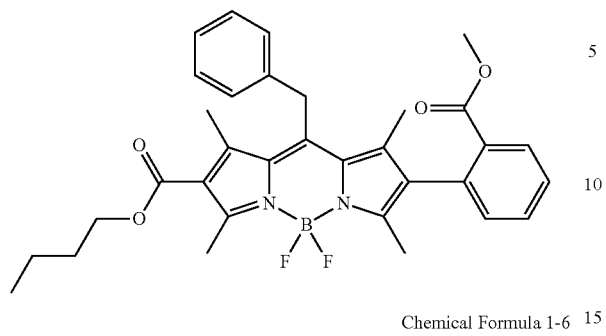
Chemical Formula 1-6
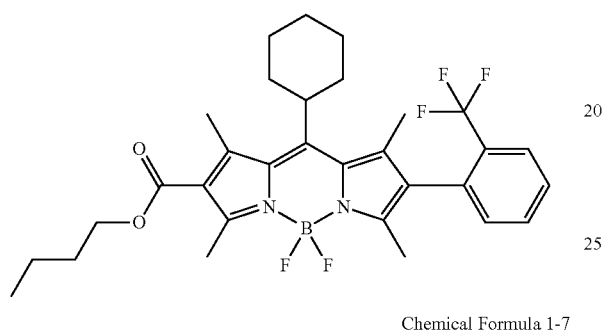
Chemical Formula 1-7
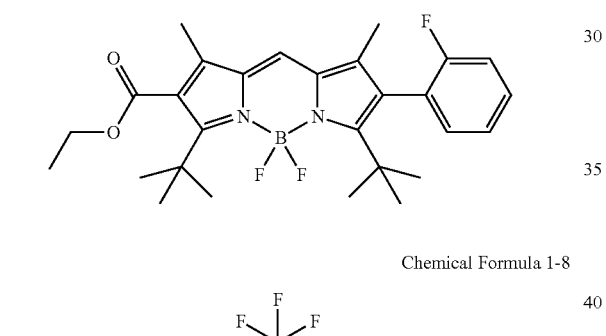
Chemical Formula 1-8
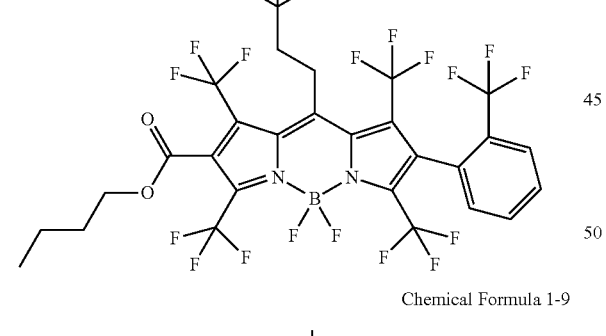
Chemical Formula 1-9
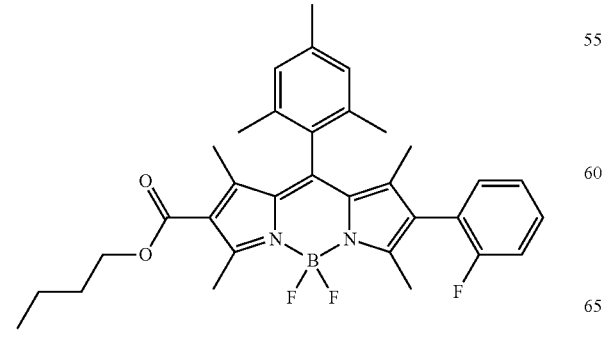
Chemical Formula 1-10
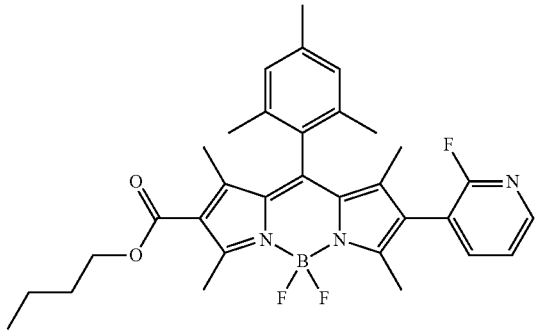
Chemical Formula 1-11
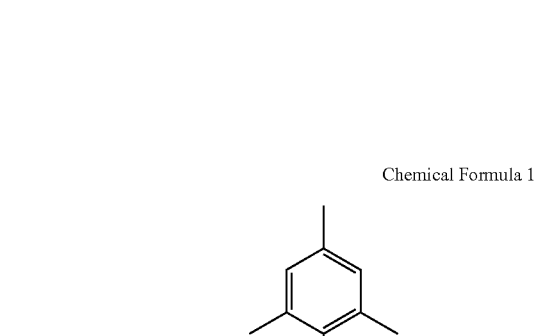
Chemical Formula 1-12
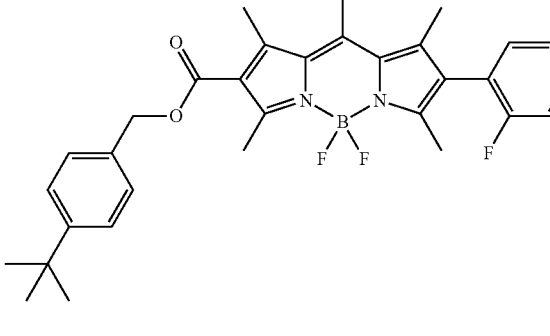

-continued
Chemical Formula 1-13
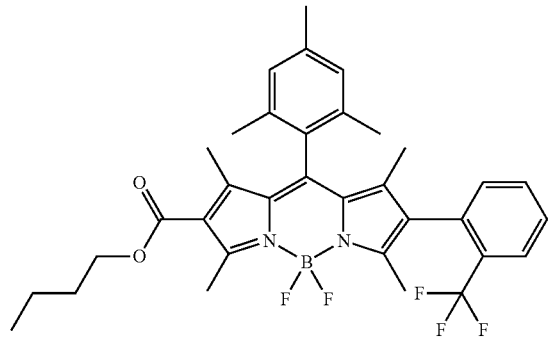
Chemical Formula 1-14
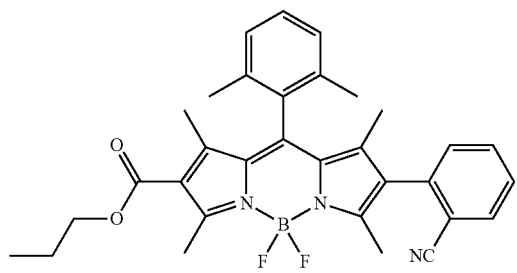
Chemical Formula 1-15
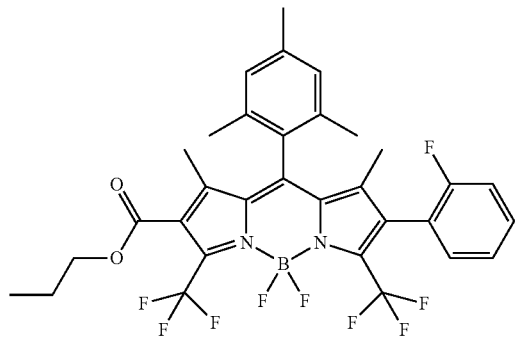
Chemical Formula 1-16
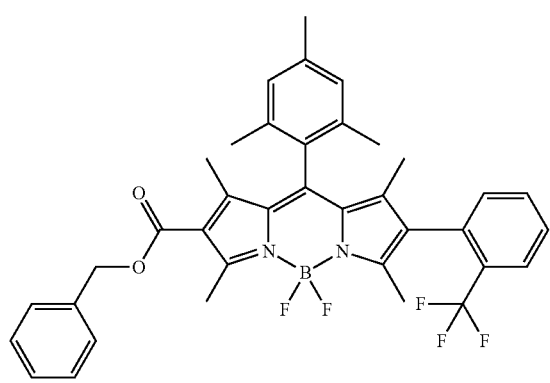
-continued
Chemical Formula 1-17
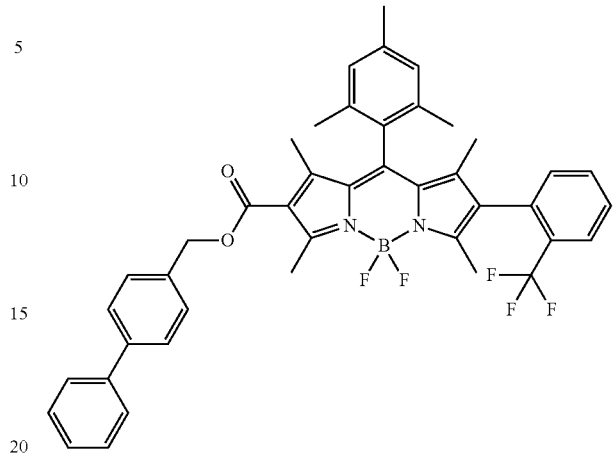
Chemical Formula 1-18
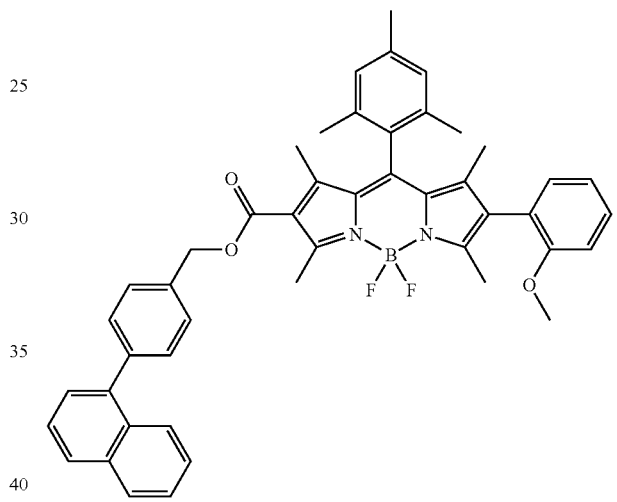
Chemical Formula 1-19
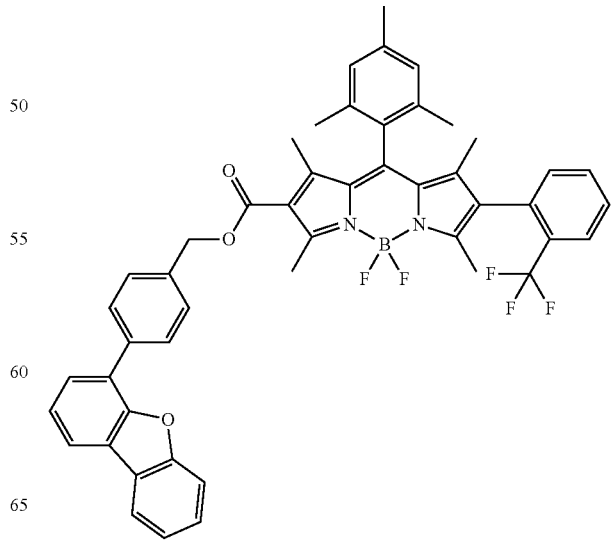

Chemical Formula 1-20
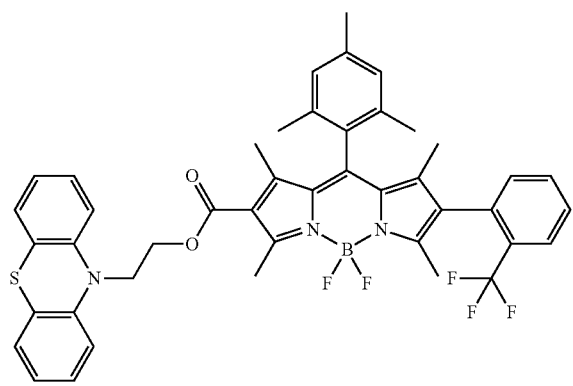
Chemical Formula 1-21
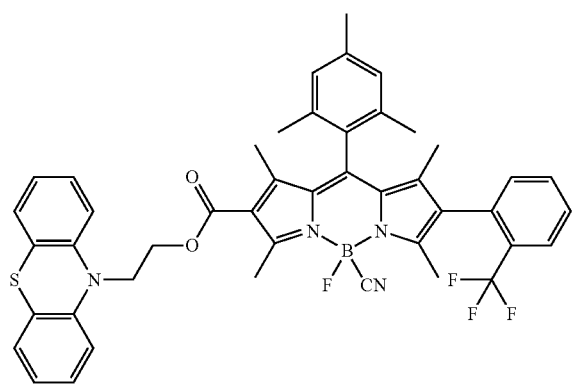
Chemical Formula 1-22
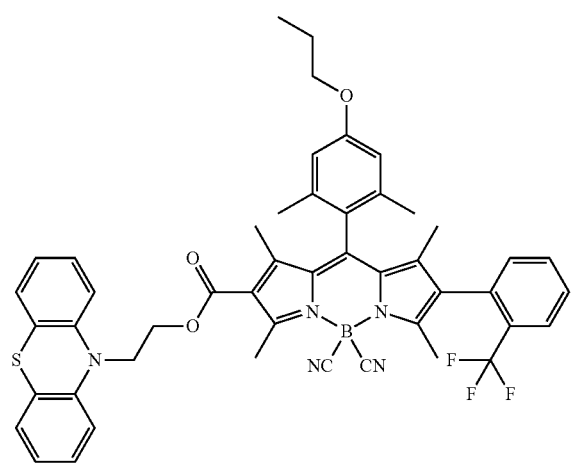
Chemical Formula 1-23
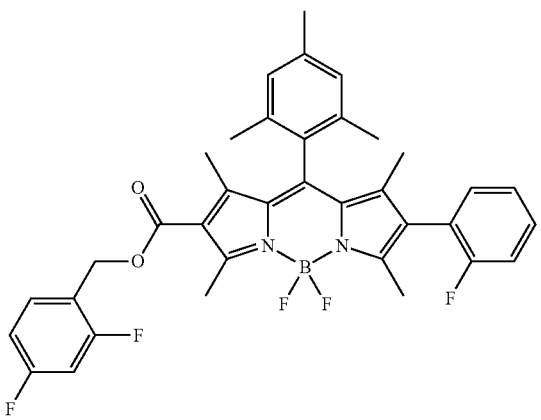
Chemical Formula 1-24
Chemical Formula 1-25
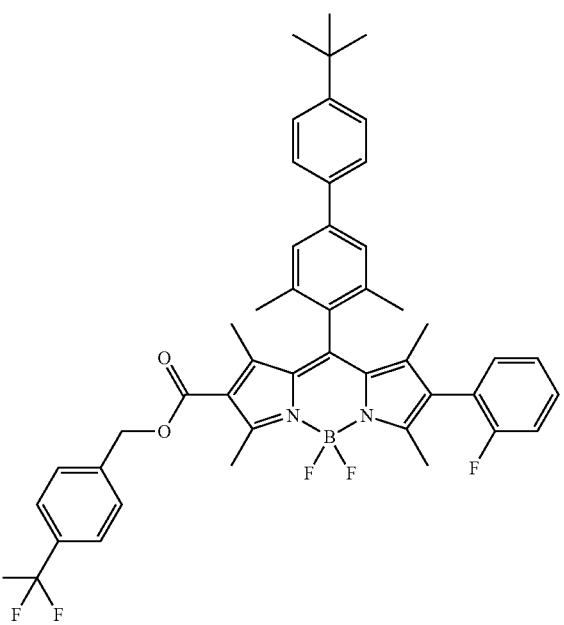

Chemical Formula 1-26
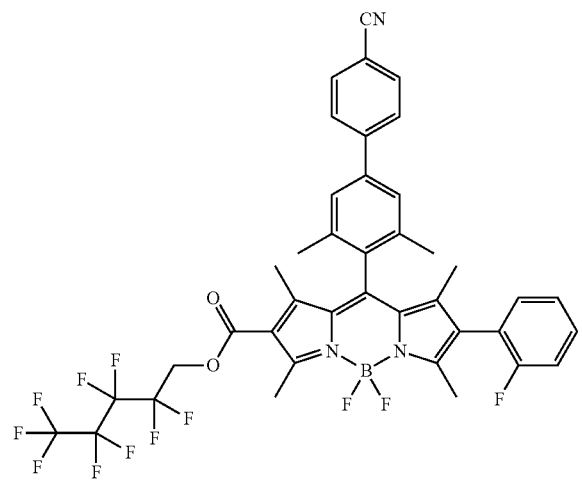
Chemical Formula 1-27
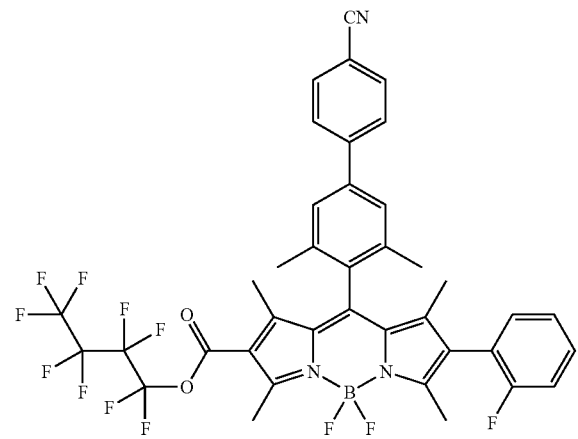
Chemical Formula 1-28
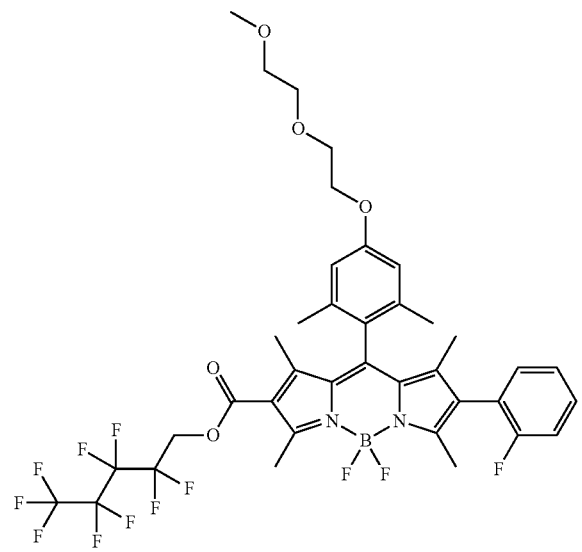
Chemical Formula 1-29
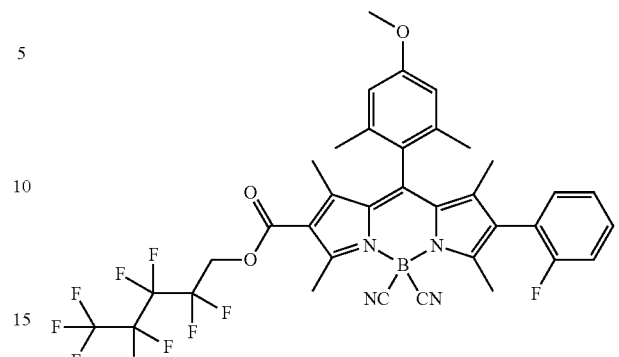
Chemical Formula 1-30
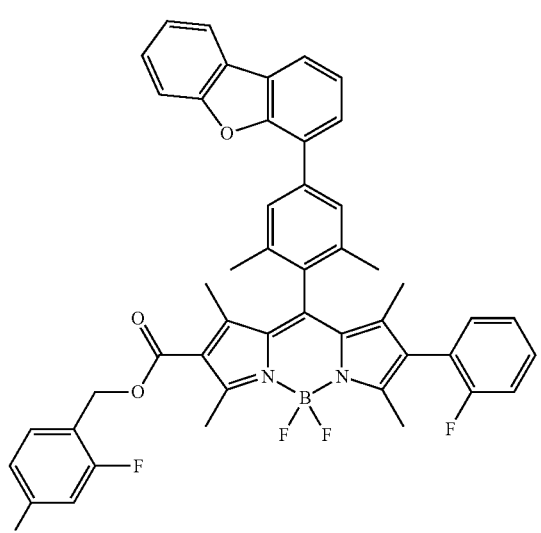
Chemical Formula 1-31
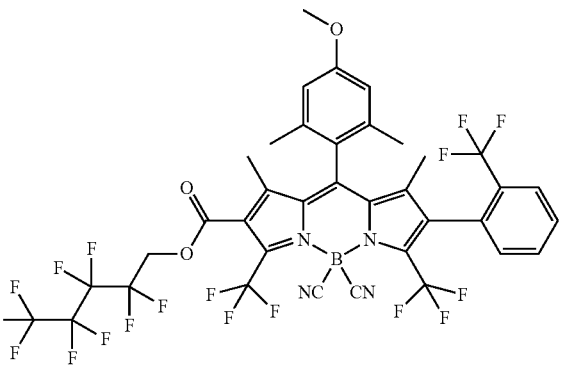

-continued
Chemical Formula 1-32
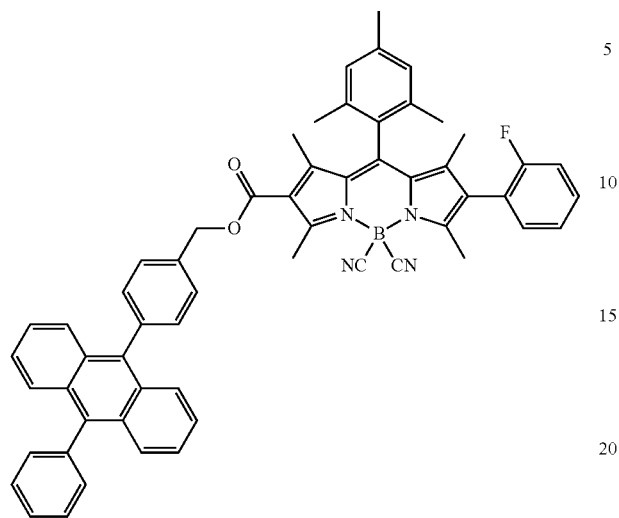
Chemical Formula 1-33
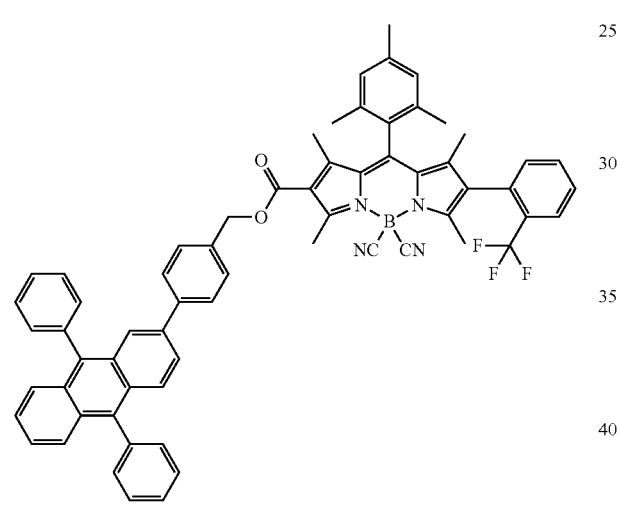
Chemical Formula 1-34
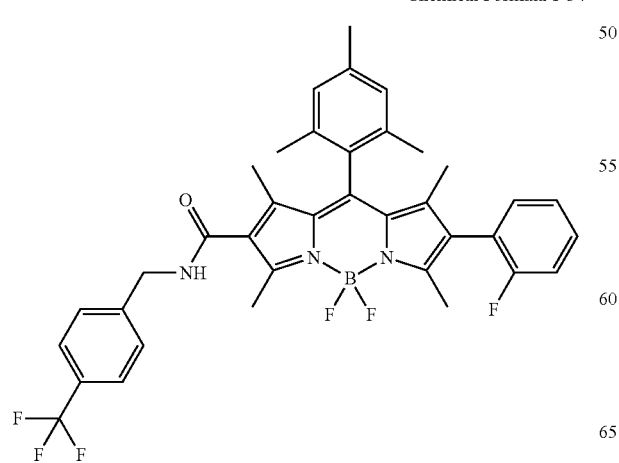
-continued
Chemical Formula 1-35
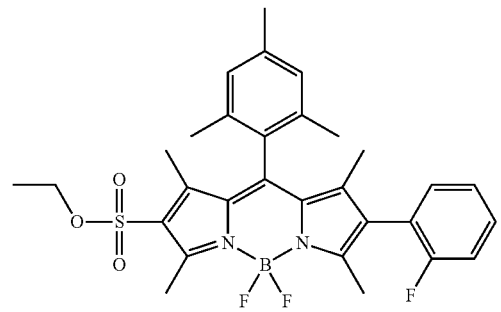
Chemical Formula 1-36
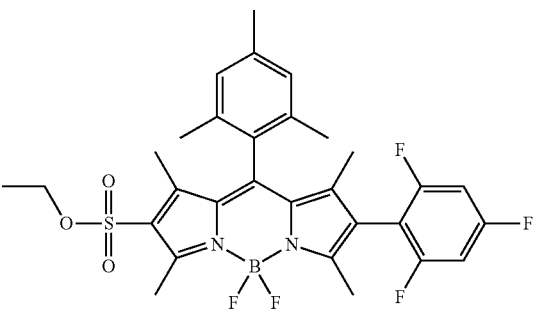
Chemical Formula 1-37
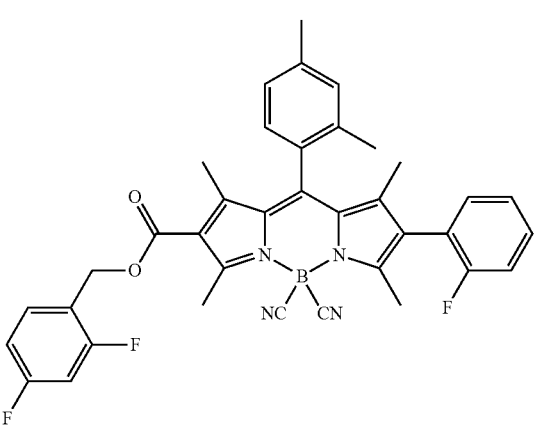
Chemical Formula 1-38
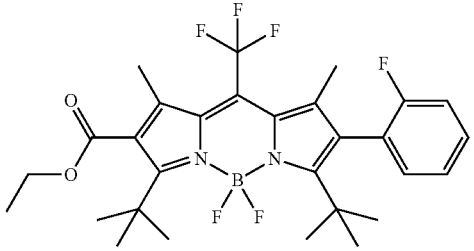

-continued
Chemical Formula 1-39
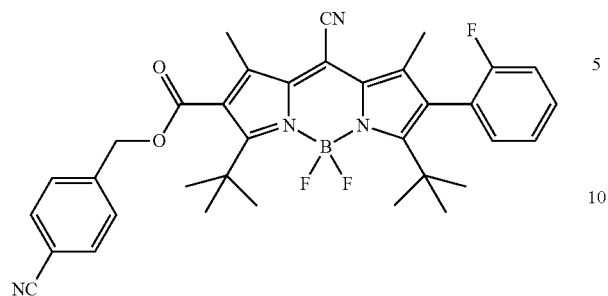
Chemical Formula 1-40
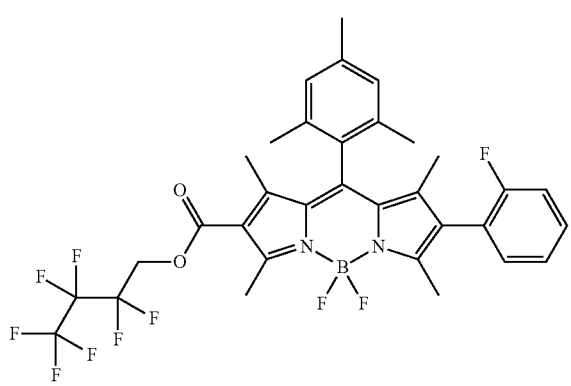
Chemical Formula 1-41
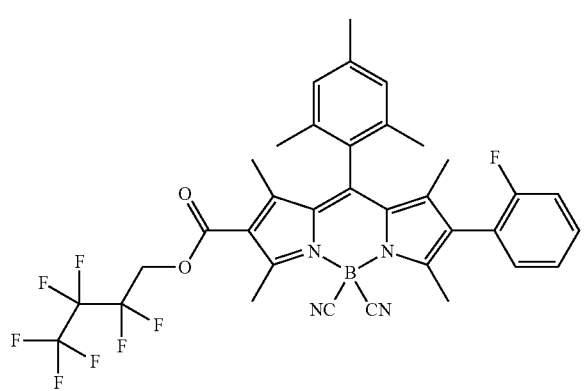
Chemical Formula 1-42
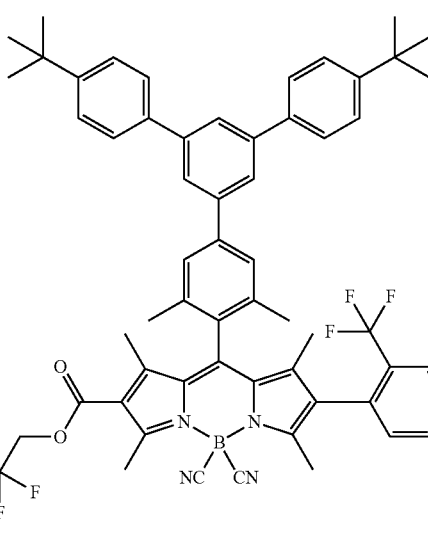
Chemical Formula 1-43
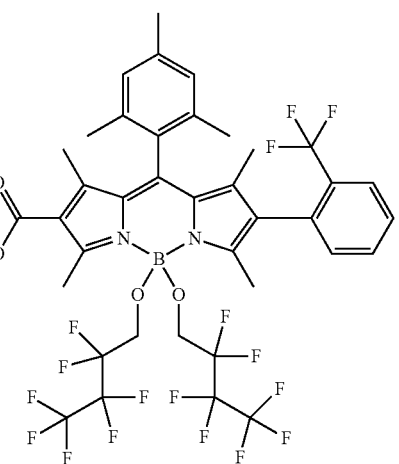
Chemical Formula 1-44
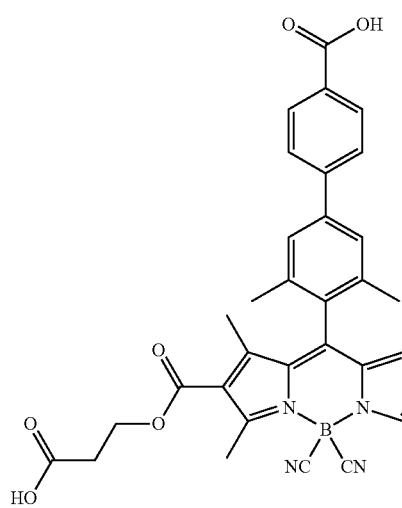

-continued
Chemical Formula 1-45
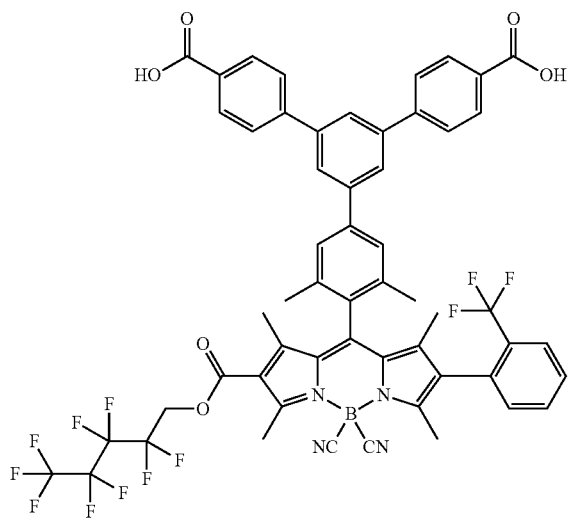
Chemical Formula 1-46
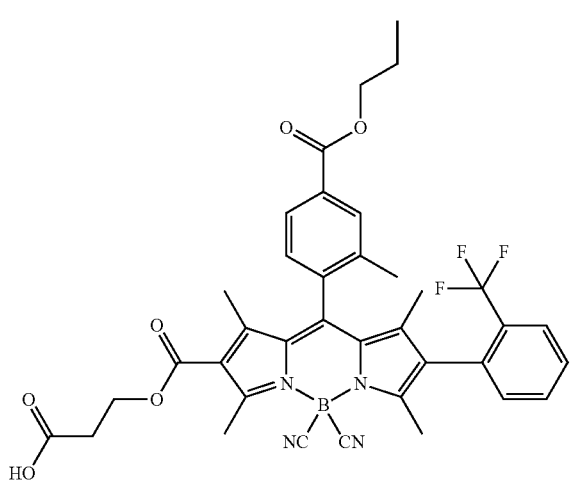
Chemical Formula 1-47
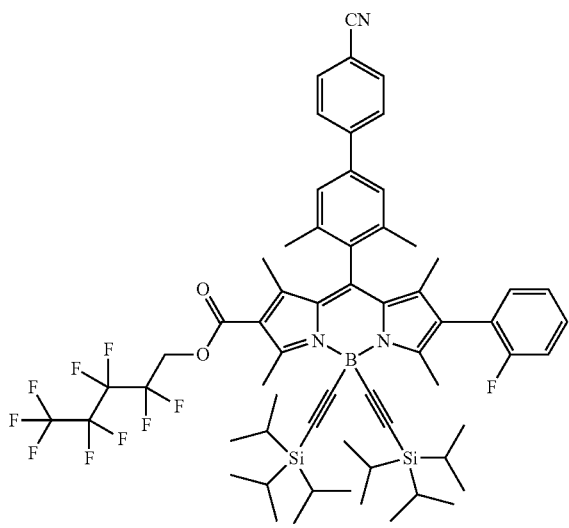
-continued
Chemical Formula 1-48
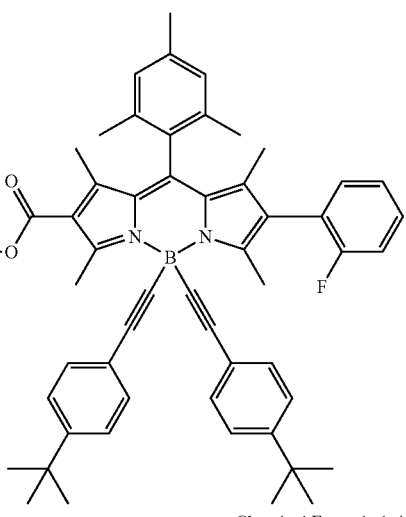
Chemical Formula 1-49
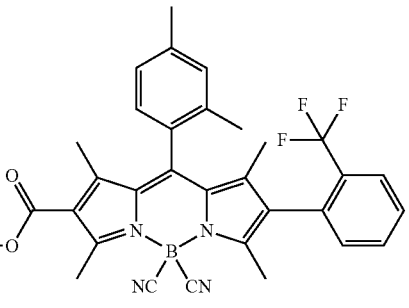
Chemical Formula 1-50
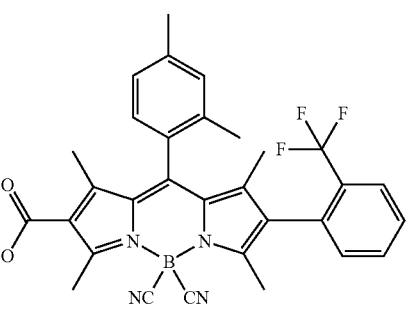
Chemical Formula 1-51
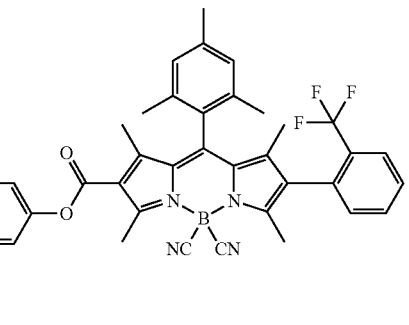

Chemical Formula 1-52
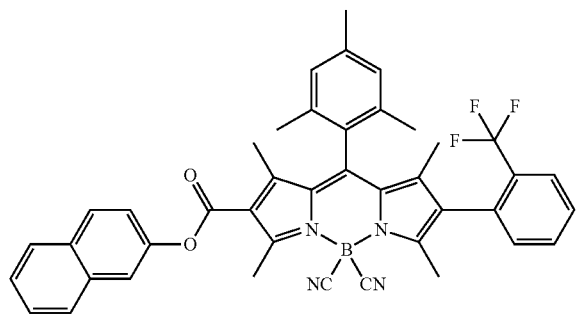
Chemical Formula 1-55
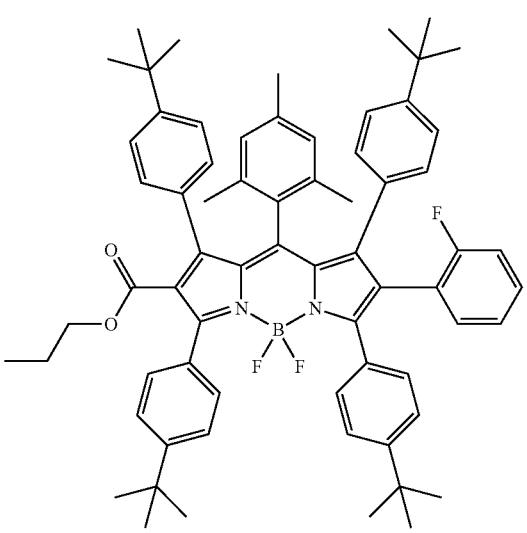
Chemical Formula 1-53
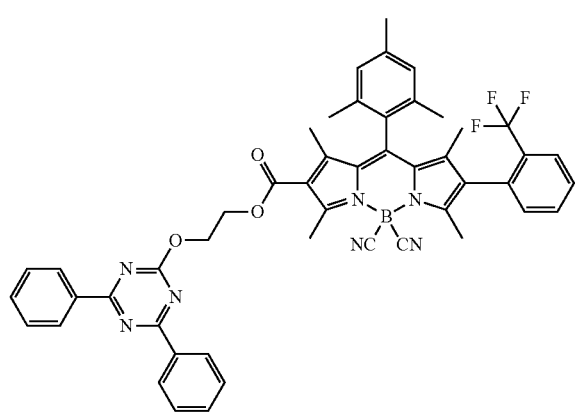
Chemical Formula 1-56
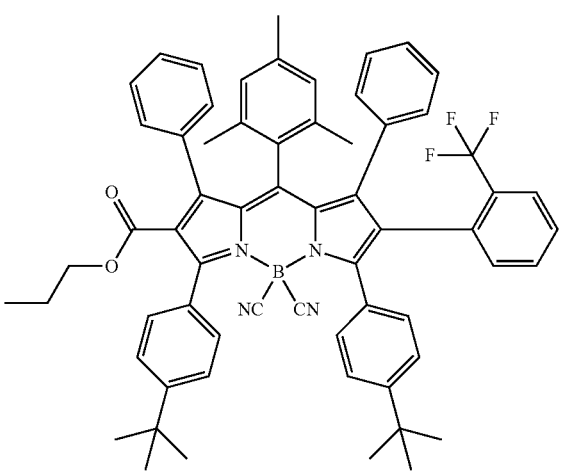
Chemical Formula 1-54
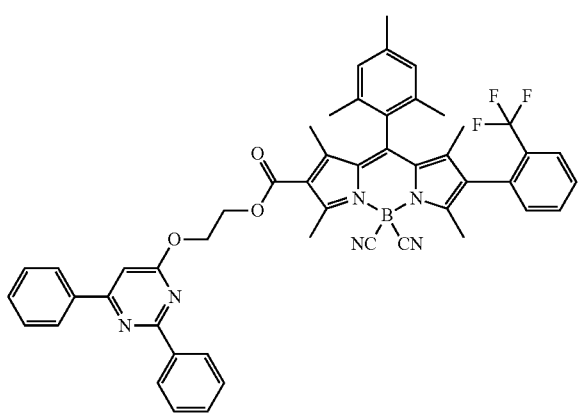
Chemical Formula 1-57
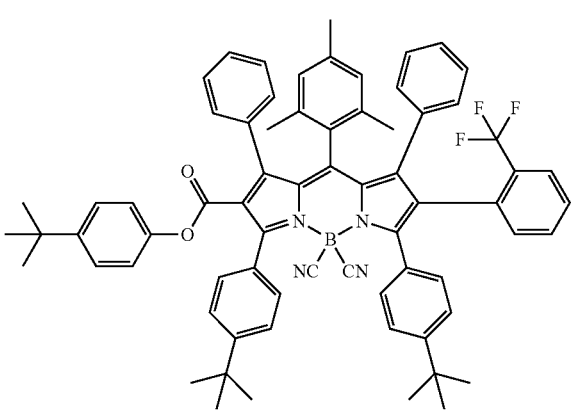

Chemical Formula 1-58
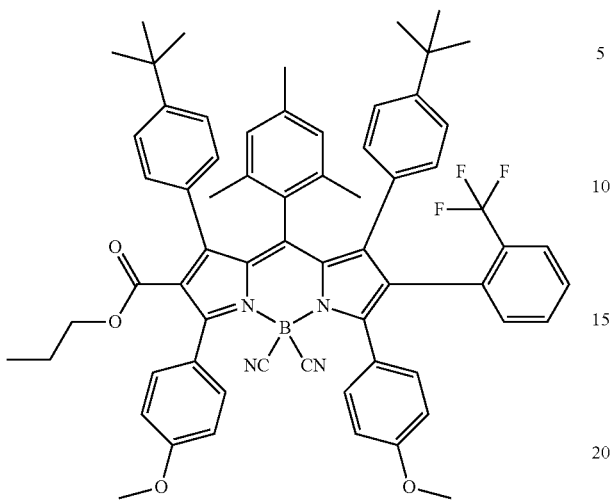
Chemical Formula 1-59
Chemical Formula 1-60
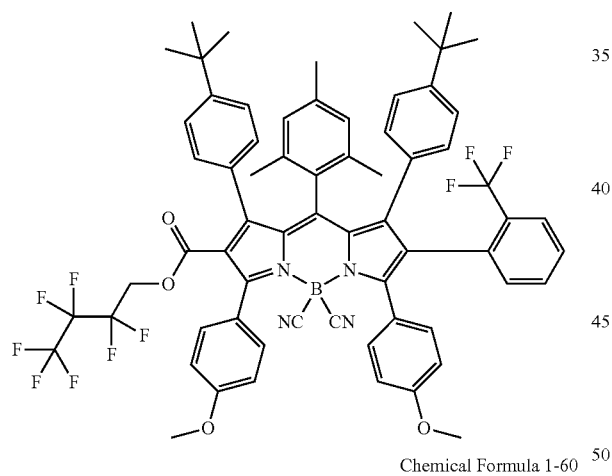
Chemical Formula 1-61
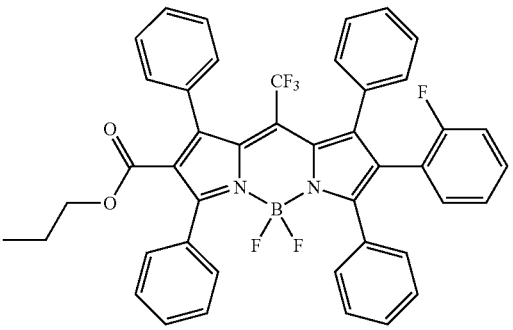
Chemical Formula 1-62
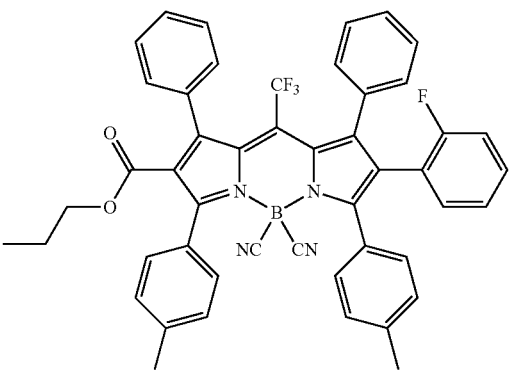
Chemical Formula 1-63
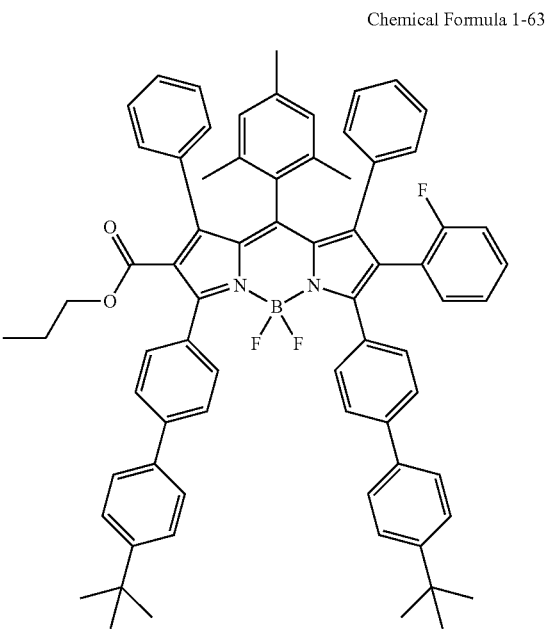

Chemical Formula 1-64
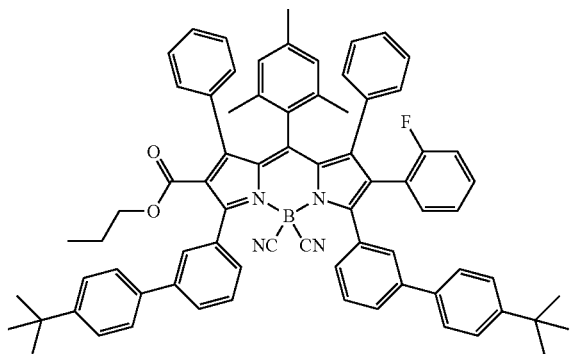
Chemical Formula 1-67
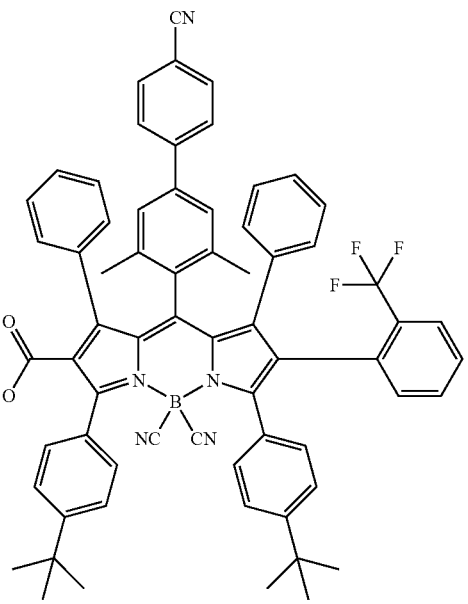
Chemical Formula 1-65
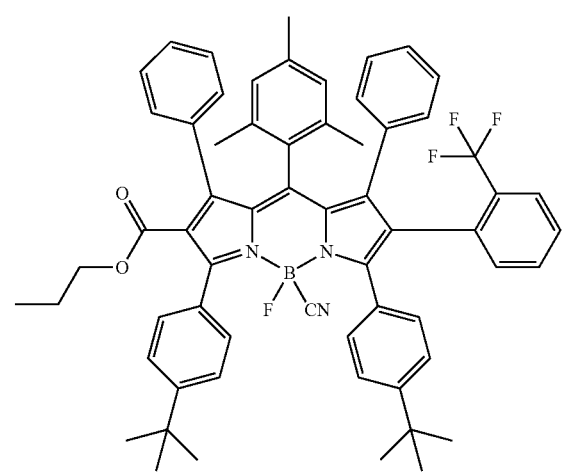
Chemical Formula 1-68
Chemical Formula 1-66
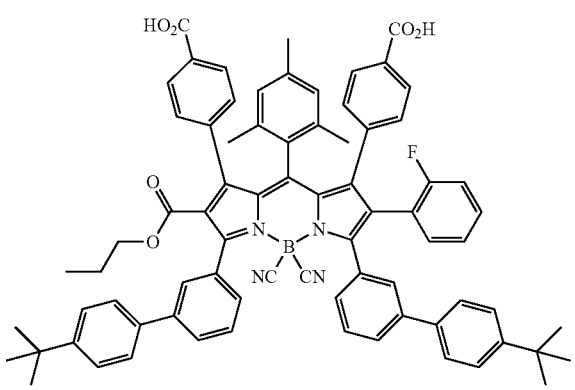
Chemical Formula 1-69
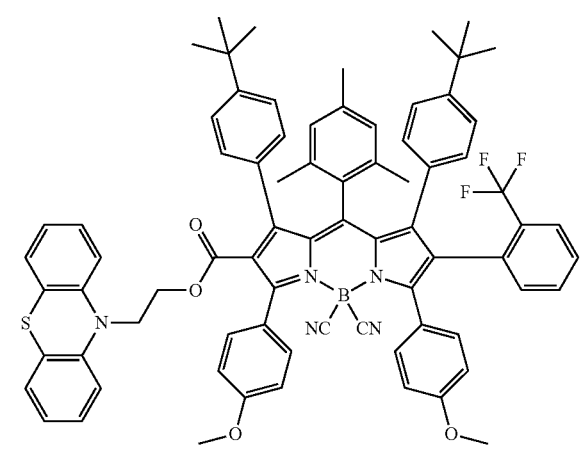

Chemical Formula 1-70
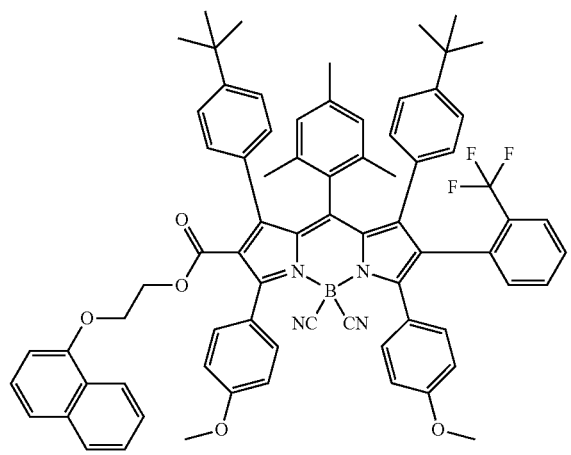
Chemical Formula 1-71
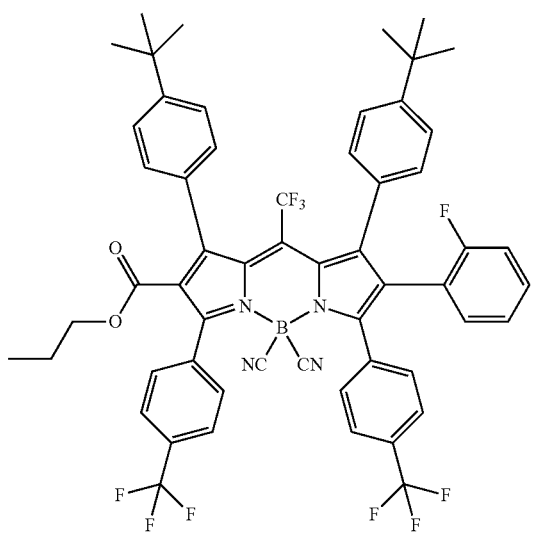
Chemical Formula 1-72
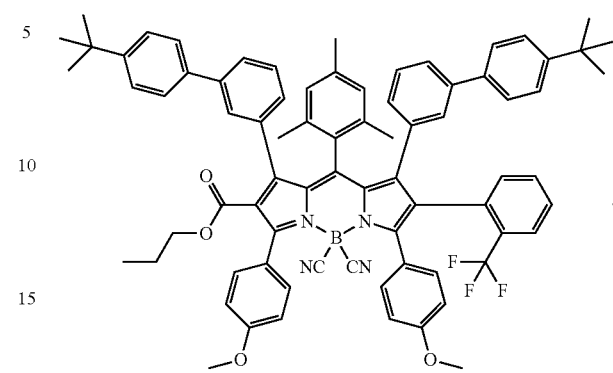
11. A color conversion film comprising:
a resin matrix; and
the compound of Chemical Formula 1 of claim 1 dispersed into the resin matrix.
12. A backlight unit comprising the color conversion film of claim 11.
13. A display device comprising the backlight unit of claim 12.
* * * * *